US009758565B2

(12) United States Patent
Peach et al.

(10) Patent No.: US 9,758,565 B2
(45) Date of Patent: Sep. 12, 2017

(54) METHODS OF TREATMENT USING CTLA4 MUTANT MOLECULES

(71) Applicant: BRISTOL-MYERS SQUIBB COMPANY, Princeton, NJ (US)

(72) Inventors: Robert James Peach, San Diego, CA (US); Joseph Naemura, Bellevue, WA (US); Peter S. Linsley, Seattle, WA (US); Jurgen Bajorath, Bonn (DE)

(73) Assignee: Bristol-Myers Squibb Company, Princeton, NJ (US)

( * ) Notice: Subject to any disclaimer, the term of this patent is extended or adjusted under 35 U.S.C. 154(b) by 267 days.

(21) Appl. No.: 14/289,715

(22) Filed: May 29, 2014

(65) Prior Publication Data

US 2015/0071914 A1 Mar. 12, 2015

Related U.S. Application Data

(60) Continuation of application No. 13/277,425, filed on Oct. 20, 2011, now Pat. No. 8,785,398, which is a division of application No. 12/694,327, filed on Jan. 27, 2010, now abandoned, which is a division of application No. 11/725,762, filed on Mar. 20, 2007, now Pat. No. 7,700,556, which is a division of application No. 10/980,742, filed on Nov. 3, 2004, now Pat. No. 7,439,230, which is a division of application No. 09/865,321, filed on May 23, 2001, now Pat. No. 7,094,874.

(60) Provisional application No. 60/287,576, filed on May 26, 2000, provisional application No. 60/214,065, filed on Jun. 26, 2000.

(51) Int. Cl.
| | | |
|---|---|---|
| *C07K 14/705* | (2006.01) |
| *A61K 38/17* | (2006.01) |
| *C07K 14/725* | (2006.01) |
| *C07H 21/04* | (2006.01) |
| *C12N 5/0783* | (2010.01) |
| *A61K 39/395* | (2006.01) |
| *A61K 38/00* | (2006.01) |
| *A61K 39/00* | (2006.01) |

(52) U.S. Cl.
CPC ...... *C07K 14/7051* (2013.01); *A61K 38/1774* (2013.01); *A61K 39/3955* (2013.01); *C07H 21/04* (2013.01); *C07K 14/70521* (2013.01); *C12N 5/0636* (2013.01); *A61K 38/00* (2013.01); *A61K 2039/505* (2013.01); *C07K 2319/30* (2013.01); *C12N 2501/51* (2013.01)

(58) Field of Classification Search
None
See application file for complete search history.

(56) References Cited

U.S. PATENT DOCUMENTS

| | | |
|---|---|---|
| 5,434,131 A | 7/1995 | Linsley et al. |
| 5,521,288 A | 5/1996 | Brady et al. |
| 5,580,756 A | 12/1996 | Brady et al. |
| 5,637,481 A | 6/1997 | Ledbetter et al. |
| 5,770,197 A | 6/1998 | Linsley et al. |
| 5,773,253 A | 6/1998 | Linsley et al. |
| 5,844,095 A | 12/1998 | Linsley et al. |
| 5,851,795 A | 12/1998 | Linsley et al. |
| 5,883,223 A | 3/1999 | Gray |
| 5,885,579 A | 3/1999 | Linsley et al. |
| 5,885,796 A | 3/1999 | Linsley et al. |
| 5,916,560 A | 6/1999 | Aruffo et al. |
| 5,958,403 A | 9/1999 | Strom et al. |
| 5,968,510 A | 10/1999 | Linsley et al. |
| 5,977,318 A | 11/1999 | Linsley et al. |
| 5,993,800 A | 11/1999 | Linsley et al. |
| 6,090,914 A | 7/2000 | Linsley et al. |
| 6,132,992 A | 10/2000 | Ledbetter et al. |
| 6,352,694 B1 | 3/2002 | June et al. |
| 6,444,792 B1 | 9/2002 | Gray et al. |
| 6,534,055 B1 | 3/2003 | June et al. |
| 6,641,809 B1 | 11/2003 | Brady et al. |
| 6,685,941 B1 | 2/2004 | Thompson et al. |
| 6,719,972 B1 | 4/2004 | Gribben et al. |
| 6,750,334 B1 | 6/2004 | Gray et al. |
| 6,830,937 B1 | 12/2004 | Brady et al. |
| 6,887,471 B1 | 5/2005 | Linsley et al. |
| 6,905,680 B2 | 6/2005 | June et al. |
| 7,030,225 B1 | 4/2006 | Tamatani et al. |

(Continued)

FOREIGN PATENT DOCUMENTS

| | | |
|---|---|---|
| CA | 2327539 A | 11/1999 |
| EP | 0 613 944 A2 | 9/1994 |

(Continued)

OTHER PUBLICATIONS

Bour-Jordan et al., Immunol Rev. May 2011 ; 241(1): 180-205.*
Malik, N. et al., "Molecular Cloning, Sequence Analysis, and Functional Expression of a Novel Growth Regulator, Oncostatin M", Molecular and Cellular Biology, vol. 9(7), pp. 2847-2853 (1989).
Merrill, J. et al., *Efficacy and Safety of Abatecept in SLE: Results of a 12-month Exploratory Study*, American College of Rheumatology, 2008 Annual Scientific Meeting (2008), http://acr.confex.com/acr/2008/webprogram/Paper3485.html.
Cunningham, B.C. et al., "Rational design of receptor-specific variants of human growth hormone", Proc. Natl. Acad. Sci. USA, vol. 88, pp. 3407-3411 (1991).

(Continued)

*Primary Examiner* — Ilia Ouspenski
(74) *Attorney, Agent, or Firm* — Nickki L. Parlet

(57) ABSTRACT

The present invention provides soluble CTLA4 mutant molecules which bind with greater avidity to the CD80 and/or CD86 antigen than wild type CTLA4 or non-mutated CTLA4Ig. The soluble CTLA4 molecules have a first amino acid sequence comprising the extracellular domain of CTLA4, where certain amino acid residues within the S25-R33 region and M97-G107 region are mutated. The mutant molecules of the invention may also include a second amino acid sequence which increases the solubility of the mutant molecule.

14 Claims, 12 Drawing Sheets

(56) References Cited

U.S. PATENT DOCUMENTS

| | | | |
|---|---|---|---|
| 7,094,874 B2* | 8/2006 | Peach | C07H 21/04 424/134.1 |
| 7,307,064 B2 | 12/2007 | Rusnak et al. | |
| 7,332,303 B2 | 2/2008 | Schilling et al. | |
| 7,541,164 B2 | 6/2009 | Schilling et al. | |
| 7,700,556 B2 | 4/2010 | Peach et al. | |
| 7,829,534 B2* | 11/2010 | Larsen | C07K 14/70521 424/134.1 |
| 2001/0053361 A1 | 12/2001 | Thompson et al. | |
| 2002/0031510 A1 | 3/2002 | Larsen et al. | |
| 2002/0039577 A1 | 4/2002 | Todderud et al. | |
| 2003/0007968 A1 | 1/2003 | Adams et al. | |
| 2003/0022836 A1 | 1/2003 | Larsen et al. | |
| 2003/0083246 A1 | 5/2003 | Cohen et al. | |
| 2003/0219863 A1 | 11/2003 | Peach et al. | |
| 2004/0014171 A1 | 1/2004 | Peach et al. | |
| 2004/0022787 A1 | 2/2004 | Cohen et al. | |
| 2011/0287032 A1* | 11/2011 | Lazar | C07K 14/70521 424/178.1 |
| 2011/0305712 A1* | 12/2011 | Akamatsu | A61K 47/48246 424/173.1 |

FOREIGN PATENT DOCUMENTS

| | | |
|---|---|---|
| EP | 0 682 029 A1 | 11/1995 |
| EP | 757099 | 5/1997 |
| WO | WO 90/05541 | 5/1990 |
| WO | WO 93/00431 | 1/1993 |
| WO | WO 93/19767 | 10/1993 |
| WO | WO 94/28912 | 12/1994 |
| WO | WO 95/01994 | 1/1995 |
| WO | WO 95/33770 | 12/1995 |
| WO | WO 95/34320 | 12/1995 |
| WO | WO 96/14865 | 5/1996 |
| WO | WO 97/34633 | 3/1997 |
| WO | WO 97/28267 | 8/1997 |
| WO | WO 97/37687 | 10/1997 |
| WO | WO 97/47732 | 12/1997 |
| WO | WO 98/31820 | 7/1998 |
| WO | WO 98/33513 | 8/1998 |
| WO | WO 98/56417 | 12/1998 |
| WO | WO 99/29883 | 6/1999 |
| WO | WO 99/47558 | 9/1999 |
| WO | WO 99/49734 | 10/1999 |
| WO | WO 99/51275 | 10/1999 |
| WO | WO 99/57266 | 11/1999 |
| WO | WO 00/23115 | 4/2000 |
| WO | WO 01/54732 A1 | 8/2001 |
| WO | WO 01/90122 A2 | 11/2001 |
| WO | WO 01/92337 | 12/2001 |
| WO | WO 02/02638 A2 | 1/2002 |
| WO | WO2004/048374 | 6/2004 |
| WO | WO 2004/058800 | 7/2004 |
| WO | WO 2004/058944 | 7/2004 |
| WO | WO 2005/016256 | 2/2005 |

OTHER PUBLICATIONS

Wells, J.A., "Binding in the growth hormone receptor complex", Proc. Natl. Acad. Sci. USA, vol. 93, pp. 1-6 (1996).
Pierce, K.H., "Growth Hormone Binding Affinity for its Receptor Surpasses the Requirements for Cellular Activity", Biochemistry, vol. 38, No. 1, pp. 81-89 (1999).
Lowman, H.B., "Affinity maturation of human growth hormone by monovalent phage display", Journal of Molecular Biology, vol. 234, pp. 564-578 (1993).
L104EA29Y (Figure 7, of the subject application) was provided to researchers at Emory University, subject to use restrictions and confidentiality by agreement, more than one year before the priority date of the subject application, i.e. May 26, 2000, for use in animal studies in the U.S.
L104EA29Y (Figure 7 of the subject application) has been the subject of human clinical trials under the direction and control of Bristol-Myers Squibb Company. L104EA29Y was given to investigators who were involved in the clinical trials subject to use restrictions and confidentiality by agreement. L104EA29Y was administered intravenously to human patients in clinical trials.
L104EA29Y was first administered intravenously to a human patient as early as Nov. 30, 1998 in Scotland.
L104EA29Y was first administered intravenously to a human patient as early as Apr. 24, 1999 in the United States.
A letter dated Jul. 9, 1998 including a report, submitted to the U.S. Food and Drug Administration in connection with an Investigational New Drug (IND) application, is enclosed as Exhibit 171.
The letter and report are confidential and were provided confidentially, pursuant to 21 C.F.R §20.111 or §21 C.F.R. §312.130, to the Center for Biologies Evaluation and Research at the U.S. Food and Drug Administration in connection with the Investigational New Drug Application.
The enclosed letter and report are redacted versions of what were sent to the U.S. Food and Drug Administration.
The report contained the sequence for BMS-224818 (Figure 3 at p. 13 of Exhibit 171), which differs from CTLA4Ig at two amine acid residues, $Leu_{104}$-Glu and $Ala_{29}$-Tyr (Exhibit 171 at p. 2).
An Investigator Brochure dated Jan. 26, 1999 is enclosed as Exhibit 172.
The Investigator Brochure is confidential and was provided to investigators who were involved in the clinical trials and subject to confidentiality by agreement, more than one year before the priority date of the subject application, i.e. May 26, 2000.
The enclosed Investigator Brochure is a redacted version of what was sent to investigators.
The Investigator Brochure contained a text description and a schematic representation of LEA29Y (Figure 1 at p. 6 of Exhibit 172), but not the sequence of L104EA29Y (Figure 7, of the subject application).
Turka et al. (1992), Proc. Natl. Acad. Sci USA 89:11102-11105 (Exhibit 24).
Lenschow et al. (1992) Science 257: 789-792 (Exhibit 25).
Linsley et al. (1992) Science 257: 792-795 (Exhibit 26).
Linsley et al. (1992) J. Exp. Med. 176:1595-1604 (Exhibit 27).
Tan et al. (1993) J. Exp. Med. 177:165-173 (Exhibit 28).
Linsley et al. (1994) Immunity 1:793-801 (Exhibit 29).
Peach et al. (1994) J. Exp. Med. 180:2049-2058 (Exhibit 30).
Steurer et al. (1995) J. Immunol. 155:1165-1174. (Exhibit 31).
Fargeas et al. (1995) J. Exp Med. 182:667-675. (Exhibit 32).
Peach et al. (1995) J. Biol. Chem. 270(36): 21181-21187. (Exhibit 33).
Alegre et al. (1995) Dig. Dis. Sci. 40(1):58-64. (Exhibit 34).
Guo et al. (1995) J. Exp. Med. 181:1345-1355. (Exhibit 35).
Rattis et al. (1996) Eur. J. Immunol. 26:449-453. (Exhibit 36).
Murakami et al. (1996) Proc. Nat. Acad. Sci. USA 93:7838-7842. (Exhibit 37).
Morton et al. (1996) J. Immol.Feb. 1; 156:1047-1054. (Exhibit 38).
Parsons et al (1996) Immunogenetics 43:3 88-391. (Exhibit 39).
Oaks et al (1996) Immunogenetics 43:172-174. (Exhibit 40).
Peach et al. (1995) Methods 8:116-123 (Exhibit 41).
Harris et al. (1997) J. Exp. Med. 185:177-182 (Exhibit 42).
Greene et al. (1996) J. Bio. Chem. 271:26762-26771 (Exhibit 43).
van der Merwe et al. (1997) J. Exper. Med. 185:393-403. (Exhibit 44).
Gallon et al. (1997) J. Immunol. 159:4212-4216. (Exhibit 45).
Höllsberg et al. (1997) J Immunol. 159:4799-4805. (Exhibit 46).
Bajorath et al. (1997) J Mol Graphics and Modeling 15:135-139. (Exhibit 47).
Greenwald et al. (1997) J Immunol. 158:4088-4096, (Exhibit 48).
Metzler et al. (1997) Nat Struc Bio 4:527-531. (Exhibit 49).
Rajesh et al. (1998) Pharm Sci Supplement S-535. (Exhibit 50).
Nuttall et al. (1999) Proteins: Structure, Functions, and Genetics 36:217-227. (Exhibit 51).
Pearson et al. (2000) Thansplantation 69:8-123, (Exhibit 52).
Reynolds et al. (2000) J Clinical Investigation. 105:643-651. (Exhibit 53).
Cinek et al. (2000) J Immunol. 164:5-8. (Exhibit 54).
Masteller et al. (2000) J Immunol. 164:5319-5327. (Exhibit 55).
Hufton et al. (2000) FEBS Letters 475:225-231. (Exhibit 56).

(56) References Cited

OTHER PUBLICATIONS

Larsen, Christian P. (2000) LEA29Y 20 Pages of Slides (Exhibit 57).
Lakkis, Fadi G., et al., "Blocking the CD28-B7 T Cell Costimulation Pathway Induces Long Term Cardiac Allograft Acceptance in the Absence of IL-4[1]," *The Journal of Immunology*, 1997, I58:2443-2448. (Exhibit 139).
Pearson, Thomas C., et al., "Analysis of the B7 Costimulatory Pathway in Allograft Rejection[1]," *Transplantation*, 1997, 63:1463-1469. (Exhibit 140).
Pearson; Thomas C., et al., "Transplantation Tolerance Induced by CTLA4-Ig[1]," *Transplantation*, 1994 57:1701-1706, (Exhibit 141).
Alexander, Diane Z., "Analysis of a Functional Role for Chimerism in CTLA4-Ig Plus Bone Marrow-Treated Cardiac Allograft Recipients,"*Transplantation*, 1994 91:416-418. (Exhibit 142).
Larsen, Christian P., et al., "CD40-gp39 Interactions Play a Critical Role During Allofraft Rejection" *Transplantation*, 1996, 61:4-9. (Exhibit 143).
Pearson, Thomas C., et at, "CTLA4-Ig Plus Bone Marrow Induces Long-Term Allograft Survival and Donor-Specific Unresonsiveness in the Murine Model", *Transplantation*, 1996, 61:997-1044. (Exhibit 144).
Weber, C.J., et al., "CTLA4-Ig Prolongs Survival of Microencapsulated Rabbit Islet Xenogidfts in Spontaneously Diabetic Nod Mice," *Transplantation Proceedings*, 1996, 28:821-823. (Exhibit 145).
Alexander, D.Z., et al., "Analysis of effector mechanisms in murine cardiac allograft rejection," *Transplantation Immunology*, 1996 4:46-48. (Exhibit 146).
Larsen, Christian P., et al., "Long-Term acceptance of skin and cardiac allografts after blocking CD40 and CD28 pathways," *Nature*, 1996, 381:434-438. (Exhibit 147).
Elwood, Eric T., et al., "Microchimerism and rejection in clinical transplantation," *The Lancet*, 1997, 349:1358-1360. (Exhibit 148).
Larsen, Christian P., and Thomas C. Pearson., "The CD40 pathway in allograft rejection, acceptance, and tolerance," *Transplantation*, 1997 9:641-647 (Exhibit 149).
Konieczny, Bogumila T;., et al., "IFN-γ Critical for Long-Term Allograft Survival Induced by Blocking the CD28 and CD40 Ligand T Cell Constimulation Pathways[1]," *The Journal of Immunology*, 1998,160:2059-2064. (Exhibit 150).
Elwood, Erie T., et al., "Prolonged Acceptance of Concordant and Discordant Xenografts With Combined CD40 and CD28 Pathway Blockade[1]," *Transplantation*, 1998,65:1422-1428. (Exhibit 151).
Niimi, Masanori, et al., "The Role of the CD40 Pathway in Alloantigen-Induced Hyporesonsiveness in Vivo[1]," *The Journal of Immunology*, 1998,161:5331-5337. (Exhibit 152).
Whitmire, Jason K., et al., "CD40-CD40 Ligand Costimulation Is Required for Generating Antiviral CD4 T Cell Responses But is Dispensable for CD8 T Cell Responses[1]," *The Journal of Immunolgy*, 1999,163:3194-3201. (Exhibit 153).
Bingaman, Adam W., et al., "Vigorous Allograft Rejection in tie Absence of Danger[1]," *Journal of Immunology*, 2000,164:3065-3071. (Exhibit 154).
Bingaman, Adam W., et al., "Transplantation of the Bone Marrow Microenvironment Leads to Hematoppietic Chimerism Without Cytoreductive Conditioning," *Transplantation*, 2000, 69:2491-2496, (Exhibit 155).
Durham, Megan M., et al., "Cutting Edge: Administration of Anti-CD40 Ligand and Donor Bone Marrow Leads to Hemapoietic Chimerism and Donor-Specific Tolerance Without Cytoreductive Conditioning[1]," *Cutting Edge*, 2000,165:1-4. (Exhibit 156).
Williams, Matthew A., et al., "Genetic Characterization of Strain Differences in the Ability to Mediate CD40/CD28-Independent Rejection of Skin Allografts[1]," *The Journal of Immunology*, 2000, 165: 6549-6857. (Exhibit 157).
Bingaman, Adam W., et al, "The role of CD40L in T cell-dependent nitric oxide production by murine macrophages," *Transplant Immunology*, 2000, 8:195-202. (Exhibit 158).

Adams, Andrew B., et al., "Costimulation Blockade, Busulfan, and Bone Marrow Promote Titratable Macrochimerism, Induce Transplantation Tolerance, and Correct Genetic Hemoglobinopathies with Minimal Myelosuppression[1], " *The Journal of Immunology*, 2001, 167:1103-1111. (Exhibit 159).
Meng, L., "Blockade of the CD40 Pathway Fails to Prevent CD8 T Cell-Mediated Intestinal Allograft Rejection," *Transplantation Proceedings*, 2001, 33: 418-420. (Exhibit 160).
Guo, Zhong., et al., "CD8 T Cell-Mediated Rejection of Intestinal Allografts Is Resistant to Inhibition of the CD40/CD154 Costimulatory Pathway," *Transplantation*, 2001, 71:1351-1354. (Exhibit 161).
Ha, Jongwon., et al., "Aggressive skin allograft rejecton in CE287 mice independent of the CD40/CD40L costimulatory pathway," *Transplant Immunology*,2001, 9:13-17. (Exhibit 162).
Bingaman, Adam W., et al., "Analysis of the CD40 and CD28 Pathways on Alloimmune Responses by CD4+ T Cells In Vivo[1], " *Transplantation*, 2001, 72:1286-1292. (Exhibit 163).
Adams, Andrew B., et al., "Calcineurin Inhibitor-Free CD28 Blockade-Based Protocol Protects Allogensic Islets in Nonhuman Primates," *Diabetes*, 2002, 51:265-270. (Exhibit 164).
Whelchel, JD., et al, "Evolving Strategies in immunosuppressive Therapy: The Emory Experience," *Clinical Transplants*, 1996, 20:249-255 (Exhibit 165).
Ritichie, SC., et al., "Regulation of Immunostimulatory function and B7 molecule expression on murine dendritic cells," *Journal of Cellular Biochemistry*, 1995,21A:C1-215(Exhibit 166).
Alexander, DZ., et al., "Analysis of the mechanisms of CTLA4-Ig plus bone marrow induced transplantation tolerance," *Journal of Cellular Biochemisty*, 1995, 21A:C1-301 (Exhibit 167).
Alexander, DZ., et al., "CTLA4-Ig induced transplantation tolerance: analysis of donor cell chimerism," *Surgical Forum*, 1994, 45:402-403 (Exhibit 168).
Pearson, TC., et al., "CTLA4-Ig plus bone marrow induces transplantation tolerance in the murine model," *Journal of Cellular Biochemistry*, 1995, 21A:C1-327 (Exhibit 169).
Lakkis, FG., et al., "CTLA4Ig induces long-term cardiac allograft survival in the absence of interleukin-4," *Journal of the American Society of Nephrology*, 1996, 7:A3204 (Exhibit 170).
Linsley, et al., 1991, *J.Exp.Med*."CTLA-4 Is a Second Receptor for the B Cell Activation Antigen B7" 174:561-569. (Exhibit 65).
Gimini, et al., 1993, *Proc.Natl.Acad.Sci. USA* "Human T-Cell clonal energy is induced by antigen presentation in the absence of B7 costimulation" 90:6586-6590. (Exhibit 66).
Azuma et al., 1993 *Nature* "B70 antigen is a second ligand for CTLA-4 and CD28" 366:76-79. (Ekhibit 67).
Ronchese et al., 1994 *J.Exp.Med* "Mice Transgenic for a Soluble Form of Murine CTLA-4Show Enhanced Expansion of Antigen-specific CD4 T Cells and Defective Antibody production In Vivo" 179;849-817. (Exhibit 68).
Griggs et al., 1996 *J.Exp.Med* "The Relative Contribution of the CD28 and gp39 Costimulatory pathways in the Clonal Expanion and Pathgenic Acquistion of Self-reactive T Cells" 183:801-810. (Exhibit 69).
Linsley et al., *J.Exp.Med* "CTLA-4 Is a Second Receptor for the B Cell Activation Antigen B7" 174:561-569. (Exhibit 70).
Verwilghen et al., 1994 *J-Immunol*. Expressionof Functional B& and CTLA4 on Rheumatoid Synovial T Cells 153:1378-1385. (Exhibit 71).
Blazer et al., 1994 *Blood* "In Vivo Blockade of CD28/CTLA4: Interaction With CTLA-Ig Reduces Lethal Murine Graft-Versus-Host Disease Across the Major Histocompatbility Complex Barrier in Mice" 83:3815-5825. (Exhibit 72).
Finck et al., *Science* "Treatment of Marine lupus with CTLA4Ig" 265:1225-1227. (Exhibit 73).
Perrin et al., 1995 *J-Immunol* "Role of B7:CD28/CTLA4 in the Induction of Chronic Relapsing Experimental Allergic Encephalomyelitis" 154:1481-1490. (Exhibit 74).
Pearson et al., 1994 *Transplantation* "Transplantation Tolerance Induced by CTLA4-Ig" 57:1701-1706. (Exhibit 75).
Baliga et al., 1994 *Transplantation* "CTLA4Ig Prolongs Allograft Survival While Suppressing Cell-Mediated Immunity" 58:1082-1090. (Exhibit 76).

(56) References Cited

OTHER PUBLICATIONS

Tapper et al., 1994 *Transplantation Proceedings* "Tolerance Induction by soluble CTLA4 in a Mouse Skin Transplant Model" 26:3151-3154. (Exhibit 77).
Perico et al., 1995 *Kidney International* "Toward novel antirejection strategies: In vivo immunosuppressive properties of CTLA4Ig" 47:241-246. (Exhibit 78).
Finck et al., 1994 *Arthritis and Rheumatism* "Effects of CTLA4Ig in murine lupus" 37:S222. (Exhibit 79).
Nishikawa et al., 1994 *Eur J. Immunol.* "Effect of CTLA-4 chimeric protein on rat autoimmune anti-glomerular basement membrane glomernlonephritis" 24:1249-1254, (Exhibit 80).
Wallace et al., 1994 *Transplantation* "CTLA4ig treatment ameliorates the lethality of murine graft-versus-host disease across major histocompatibility complex barriers" 58:602-610. (Exhibit 81).
Damle et al., *J. Immunol.* "Costimulation of T Lymphocytes with integrin Ligands intercellular Adhesion Molecule-1 or Vascular Cell Adhesion Molecule-1 Induces Functional Expression of CTLA-4, a Second Receptor for B7" 152:2686-2697. (Exhibit 82).
Milich, et al., 1994. *J. Immunol* "Soluble CTLA-4 can suppress autoantibody production and elicit long term unresponsiveness in a novel transgenic model," 153:429-435. (Exhibit 83).
Webb, et al., 1996 *Eur J. Immunol* "Prevention and amelioration of collagen-induced arthritis by blockade of the CD28 co-stimulatory pathway: requirement for both B7-1 and B7-2," 26:2320-2328. (Exhibit 84).
Van Oosterhout, et al., 1997 *Am.J.Respir.Cell Mol.Biol* ."Murine CTLA4-IgG. Treatment Inhibits Airway Eosinophilia and Hyper-responsiveness and Attenuates IgE Upregulation in Murine Model of allergic Asthma," 17:386-392. (Exhibit 85).
Abams et al., 1999 *J-Clin-Invest* CTLA4Ig-mediated blockade of T-cell costimuation in patients with psoriasis vulgaris. 303:1243-1252. (Exhibit 86).
Ibrahim, et al., 1996 *Blood* "CTLAIG Inhibits Alloantibody Responses to Repeated Blood Transfusions," 88:4594-4600. (Exhibit 87).
Lenschow, et al., 1995 *J Exp Med* "Differential Effects of anti-B7-1 and Anti-b&-2 Monoclonal Antibody Treatment on the Development of Diabetes in the Nonobese Diabetic Mouse," 181:1145-1155 (Exhibit 88).
Lenschow, et al., 1992 *Science* "Long-Term Survival of Xenogeneic Pancreatic islet Grafts Induced by CTLA4Ig," 257:789-792. (Exhibit 89).
Blazer, et al., 1994 *Blood* "In Vivo Bloakade of CD28/CTLA4:B7/BB1 Interaction with CTLA4-Ig Reduces Lethal Marine Graft-Versus-Host Disease Across the Major Histocompatibility Complex Barrier in Mice," 83:3815-3825. (Exhibit 90).
Griggs, et al., 1996 *J Exp Med* "The relative Contribution of the CD28 and gp39 Costimulatory pathways in the Clonal Expansion and Pathogenic Acquisition of Self-reactive T Cells," 183:801-810, (Exhibit 91).
Sayegh., 1999 *J Clin Invest* "Finally, CTLA4Ig graduates to the clinic," 103:1223-1225. (Exhibit 92).
Abrams, et al., 1999 *J Clin Invest* "CTLAIg-mediated blockade of T-cell costimulation I patients with psoriasis vulgaris," 103:1243-1252, (Exhibit 93).
Wolfe, 1995 *Bailliere's Clinical Rheumatology* "The epidemiology of drug treatment failure in rheumatoid arthritis," 9:619-637 (Exhibit 94).
Hochberg, et al., 1990 *Epidemiologic Reviews* "Epidemiology of Rheumatoid Arthritis: Update," 12:247-252. (Exhibit 95).
Spector, 1990 *Epidemiology of Rheumatic Disease* "Rheumatoid Arthritis," 16:513-537. (Exhibit 96).
Liu MF, Kohsaka H Sakurai H, Azuma m Okumura K Saito I, Miyasaka N, 1996. "The presence of costimulatory molecules B7.1 (CD80) and B7.2 (CD86) in rheumatoid arthritis synovium" *Arthritis-Rheum.*, Jan.; 39(1): 110-4. (Exhibit 97).

Sfikakis PP, Via CS. 1997 "Expression of CD28, CTLA4, CD80, CD86 molecules in-patients with autoimmune rheumatic diseases: implications for immunotherapy". *Clin-Immunol-Immunopathol.* Jun.; 83(3): 195-8. (Exhibit 98).
Sayegh MH, Akabn E, Hancock WW, Russell ME, Carpenter CB, Linsley PS, Turka LA, 1995. *J Exp. Med.* "CD28-B7 blockade after allantigenic challenge in vivo inhibits Th1 cytokines but spares Th2". 181:1869-1874. (Exhibit 99).
Racusen LC; et. al. 1999. "The Baniff 97 working classification of renal allograft pathology". *Kidney-Int.* 55(2): 713- 723. (Exhibit 100).
Parkin D, Jacoby A, McNamme P, 2000, "Treatment of multiple sclerosis with interferon β: an appraisal of cost-effectiveness and quality of life" *J Neurol Neurosurg Psychiatry*; 68: 144-149. (Exhibit 101).
Nortvedt MW, Riise T, Mybr KM, and Nyland HI, 1999. "Quality of life in multiple sclerosis: measuring the disease effects more broadly" Neurology; 53(5): 1098-1103 (Exhibit 102).
Pearson TC, Alexander DZ, Winn KJ, Linsley PS, Lowry RP, Larsen CP, 1994. Transplantation tolerance induced by CTLA4-Ig. *Transplantation*, 57:1701-1706. (Exhibit 103).
Liao HX, Hames BF, 1995. "Role of adhesion molecules in the pathogensis of rheumatoid arthritis" *Rheum-Dis-Clin-Noth-Am.* Aug. 21(3): 715-40. (Exhibit 104).
Thomas R, Quinn C. 1996. "Functional differentiation of dendritic cells in rheumatoid arthritis: role of CD86 la the synovium" *J-Immunol.* Apr. 15; 156(3); 3074-86. (Exhibit 106).
Verboeven-AC; Boers-M; Tugwell-P, 1998. "Combination therapy in rheumatoid arthritis: updated systematic review" *Br-J-Rheumatol.* Jun.;37 (6): 612-619 (Exhibit 107).
Schiff M, 1997. "Emerging treatments for rheumatoid arthritis" *Am-J-Med.* Jan. 27; 102 (1A): 11S-15S (Exhibit 108).
Balsa A,- Dixey-J, Sansom DM,- Maddison PJ, Hall ND, 1996. "Differential expression of the costimulatory molecules B7.1 (CD80) and B7.2 (CD86) in rheumatoid synovial tissue" *Br-J-Rheumatol*, Jan.; 35(1): 33-7 (Exhibit 109).
Ranheim Ea, Kipps Tj, 1994. "Elevated expression of CD80 (137/BB1) and other accessory molecules on synovial fluid mononuclear cell subsets in rheumatoid arthritis" *Arthritis-Rheum.* Nov.;37 (1I): 1637-1647 (Exhibit 110).
Freeman GJ, Gribben JG, Boussiotis VA, et al. 1993, "Cloning of B7-2: a CTLA-4 counter receptor that costimulates human T cell proliferation" *Science*, 262: 909-911. (Exhibit 111).
Baliga P, Chavin KD, Qin L, et al. "CTLA4Ig prolongs allograft survival while suppressing cell-mediated immunity" *Transplantation*, 58(10): 1082-1090. (Exhibit 112).
Thomas R, Quinn C, 1996 "Functional differentiation of dendritic cells in rheumatoid arthritis: role of CD86 in the synovium" *J-Immunol.* Apr. 15;156(8): 3074-86 (Exhibit 113).
Becker, J.C.,Mar. 8, 2001, Abstract and of Presentation of "A multi-center, randomized, double-blind, placebo controlled study to evaluate the safety and preliminary clinical activity of multiple doses of CTLA4Ig and LEA29Y administration intravenously to subjects with rheumatoid arthritis," presented at American College of Rheumatology Conference: "2001 Innovative Therapies in Autoimmune Diseases," San Francisco, California (Exhibit 114).
Aruffo, S., Mar. 27, 2000, Presentation of "Approaches to Immune Regulation" at BIO 2000 in Boston, Mass. (Exhibit 115).
Abrams, et al., Sep. 4, 2000, *J.Exp.Med.* "Blockade of T Lymphocyte Costimulation with Cytotoxic T Lymphocyte-associated Antigen 4-Immunogloblin (CTLA4Ig) Reverse the Cellular Pathology of Psoriatic plaques, Including the Activation of Keratinocytes, Dendritic Cells, and Endothelial Cells," 192:60-693. (Exhibit 116).
Srinivas, N.R. et al., Dec. 1, 1995, *J.Pharmaceutical Sciences* "Pharmacokinetics and pharmacodynainics of CTLA4Ig (BMA-188667), a Novel Immunosuppressive Agent, in Monkeys following Multiple Doses," 85:1-4. (Exhibit 117).
Gandhi, et al., Nov. 18, 1998, Abstract and Presentation of *Pharm Sci Supplement* "Physical and Chemical Characterization of BMS-224818, A Recombinant Fusion Protein," in San Francisco, Ca. (Exhibit 118).

(56) References Cited

OTHER PUBLICATIONS

Flesher, A.R., Apr. 15, 1999, *Biological Process Sciences* Presentation of Transgenic Production, A Comparative Study at Bio 99 in Seattle, Washington. (Exhibit 119).

Greve, K.F., May 9, 1996, J Chromatography, "Capillary electrophoretic examination of underivatized oligosaccharide mixtures released from immunoglobulin G antitbodies and CTLA4Ig fusion protein," 749:237-245. (Exhibit 120).

Srinivas, N.R., Apr. 8, 1997, *Pharmaceutical Research* "Assessment of Dose Proportionality, Absolute Bioavailability, and Immunogenicity Response of CTLAIg (BMS-188667), a Novel Immunosuppressive Agent, Following Subcutaneous and Intravenous Administration to Rats" 14:911-916. (Exhibit 121).

Weiner, R.S., Nov. 6-10, 1994, Abstract and Presentation of "Validation and PK Application of a Double Antibody Sandwich Enzyme Immunoassay For the Quantitation of Human CTLAIg Fusion Protein (BMS-188667) In Mouse Serum," (Exhibit 122).

Weiner, R.S., Jun. 6, 1996, *J Pharmaceutical and Biomedical Analysis* "A sensitive enzyme immunoassay for the quantitation of human CTLA4Ig fusion protien in mouse serum: pharmacokinetic application to optimizing cell line selection," 15:571-579. (Exhibit 123).

Warner, G.I. et al., Mar. 16-22, 1995, Abstract and Presentation of "Bioactivity of BMS-188667 (CTLAIg) in Cynomolgus Monkeys," in Seattle, Washington. (Exhibit 124).

Weiner, R.S., Mar. 1, 2000, Abstract and Presentation of "Industrial Perspectives of Primary Analytical Tools for Macromaloecules—Principles and Applications with Examples." (Exhibit 125).

Weiner, R.S., Nov. 1995 Abstract and Presentation of "Validation of an Enzyme Immunoassay For The Quantition of Human CTLA1g Fusion Protein in Human Serum," in Miami, Florida (Exhibit 126).

Weiner, R.S., Nov. 1995 Abstract and Presentation of "Automation and Validation of An EIA For Quantition of Human CTLAIg In Monkey Serum," in Miami, Florida (Exhibit 127).

Webb, L.M.C. et al., Jul. 23, 1996 *Eur J Immunol* "Prevention and amelioration of collagen-induced arthritis by blocade of the CE28 co-stimulatory pathway requirement far both B7-1 and B7-2" 26:2320-2328. (Exhibit 128).

Knoerzer, et al., May 5, 1995, *J Clin. Invest* "Collagen-induced Arthritis in the BB Rat Prevention of Disease by Treatment with CTLA4Ig" 96:987-993. (Exhibit 129).

Larsen, et al., Apr. 27, 2000, Abstract of "Prolongation of Renal Allograft Survival wits Blockade of the CD28 Pathway Using A Novel Mutant CTLA4-IG Fusion Protein in Non-Human Primates," in *Transplantation*, 69(8):#44, p. S123, Chicago, Il. (Exhibit 130).

Larsen, et al., May 13-17, 2000, A Presentation of "Prolongation of Renal Allograft Survival With Blockade of the CD28 Pathway Using A Novel Mutant CTLA4-Ig Protein in Nonhuman Primates" at the American Society of Transplantation Meeting in Chicago, Il. (Exhibit 131).

Larsen, Aug. 27-Sep. 1, 2000, A Presentation of "Manipulation of Costimulatory Pathways: Targeting CD80 and CD86" at the XVII congress of the Transplantation Society in Rome, Italy. (Exhibit 132).

Larsen, Mar. 3-4, 2000, A Presentation of "Costimulation blockade: progress toward clinical application" at Canadian Society of Transplantation Annual Scientific meeting in Mont Tremblant, Quebec, Canada. (Exhibit 133).

Larsen, Jan. 13-17, 2000, A Presentation of "Costimulation blockade: Progress toward clinical application" at the American Society of Transplantation Meeting in Las Croabas, Puerto Rico. (Exhibit 134).

Hathcock, et al., Aug. 30, 1993 *Science* "Identification of an Alternative CTLA-4 Ligand Costimulatory for 1 Cell Activation," 262:905-911. (Exhibit 135).

Sfikakis, et al., Nov. 29, 1994 *Arthritis & Rheumatism* "CD28 Expression On T Cell Subsets in Vivo And CD28-Mediated T Cell Response In Vitro In Patients With Rheumatoid Arthritis," 38:649-654. (Exhibit 136).

Sun, Hong et al., "Prevention of Chronic Rejection in Mouse Aortic Allografts by Combined Treatment with CTLA4-Ig and Anti-CD40 Ligand Monoclonal Antibody," Transplantation; 1997, 64:1838-56 (Exhibit 177).

Souza, "Synergistic inhibition of established collagen induced arthritis (CIA) through dual inhibition of ICAM-I and CD40L pathways" *Arthritis and Rhuematism*, 1999, p. S60; abstract 64 (Exhibit 178).

Blazar, Bruce R. et al., "Coblockade of the LFA.1:ICAM and CD28/CTLA4:B7 Pathways Is A Highly Effective Means of Preventing Acute Lethal Graft-Versus-Host Disease Induced by Fully Major Histocompatibility Complex-Disparate Donor Grafts," Blood, 1995, 85:2607-18 (Exhibit 179).

Najafian, et al., "CTLA4-Ig: a novel immunosuppressive agent," *Exp. Opin. Invest. Drugs*, 2000, 9:2147-2157 (Exhibit 181).

Schartz, R., "Consitimulation of T Lymphocytes: The Role of CD28, CTLA-4, and B7/BB1 in Interleukin-2.Production and Immunotherapy," *Cell*, 1992, 71:1085-1058. (Exhibit 194).

* cited by examiner

FIG. 7

```
ATGGGTGTACTGCTCACACAGAGGACGCTGCTCAGTCTGGTCCTTGCACTCCTGTTTCCA      -19
M--G--V--L--L--T--Q--R--T--L--L--S--L--V--L--A--L--L--F--P--      -7

AGCATGGCGAGCATGGCAATGCACGTGGCCCAGCCTGCTGTGGTACTGGCCAGCAGCCGA      +42
S--M--A--S--M--A--M--H--V--A--Q--P--A--V--V--L--A--S--S--R--      +14
                      +1

GGCATCGCTAGCTTTGTGTGTGAGTATGCATCTCCAGGCAAAGCCACTGAGGTCCGGGTG      +102
G--I--A--S--F--V--C--E--Y--A--S--P--G--K--A--T--E--V--R--V--      +34

ACAGTGCTTCGGCAGGCTGACAGCCAGGTGACTGAAGTCTGTGCGGCAACCTACATGATG     +162
T--V--L--R--Q--A--D--S--Q--V--T--E--V--C--A--A--T--Y--M--M--     +54

GGGAATGAGTTGACCTTCCTAGATGATTCCATCTGCACGGGCACCTCCAGTGGAAATCAA     +222
G--N--E--L--T--F--L--D--D--S--I--C--T--G--T--S--S--G--N--Q--     +74

GTGAACCTCACTATCCAAGGACTGAGGGCCATGGACACGGGACTCTACATCTGCAAGGTG     +282
V--N--L--T--I--Q--G--L--R--A--M--D--T--G--L--Y--I--C--K--V--     +94

GAGCTCATGTACCCACCGCCATACTACGAGGGCATAGGCAACGGAACCCAGATTTATGTA     +342
E--L--M--Y--P--P--P--Y--Y--E--G--I--G--N--G--T--Q--I--Y--V--     +114

ATTGATCCAGAACCGTGCCCAGATTCTGATCAGGAGCCCAAATCTTCTGACAAAACTCAC     +402
I--D--P--E--P--C--P--D--S--D--Q--E--P--K--S--S--D--K--T--H--     +134

ACATCCCCACCGTCCCCAGCACCTGAACTCCTGGGGGGATCGTCAGTCTTCCTCTTCCCC     +462
T--S--P--P--S--P--A--P--E--L--L--G--G--S--S--V--F--L--F--P--     +154

CCAAAACCCAAGGACACCCTCATGATCTCCCGGACCCCTGAGGTCACATGCGTGGTGGTG     +522
P--K--P--K--D--T--L--M--I--S--R--T--P--E--V--T--C--V--V--V--     +174

GACGTGAGCCACGAAGACCCTGAGGTCAAGTTCAACTGGTACGTGGACGGCGTGGAGGTG     +582
D--V--S--H--E--D--P--E--V--K--F--N--W--Y--V--D--G--V--E--V--     +194

CATAATGCCAAGACAAAGCCGCGGGAGGAGCAGTACAACAGCACGTACCGTGTGGTCAGC     +642
H--N--A--K--T--K--P--R--E--E--Q--Y--N--S--T--Y--R--V--V--S--     +214

GTCCTCACCGTCCTGCACCAGGACTGGCTGAATGGCAAGGAGTACAAGTGCAAGGTCTCC     +702
V--L--T--V--L--H--Q--D--W--L--N--G--K--E--Y--K--C--K--V--S--     +234

AACAAAGCCCTCCCAGCCCCCATCGAGAAAACCATCTCCAAAGCCAAAGGGCAGCCCCGA     +762
N--K--A--L--P--A--P--I--E--K--T--I--S--K--A--K--G--Q--P--R--     +254

GAACCACAGGTGTACACCCTGCCCCCATCCCGGGATGAGCTGACCAAGAACCAGGTCAGC     +822
E--P--Q--V--Y--T--L--P--P--S--R--D--E--L--T--K--N--Q--V--S--     +274

CTGACCTGCCTGGTCAAAGGCTTCTATCCAAGCGACATCGCCGTGGAGTGGGAGAGCAAT     +882
L--T--C--L--V--K--G--F--Y--P--S--D--I--A--V--E--W--E--S--N--     +294

GGGCAGCCGGAGAACAACTACAAGACCACGCCTCCCGTGCTGGACTCCGACGGCTCCTTC     +942
G--Q--P--E--N--N--Y--K--T--T--P--P--V--L--D--S--D--G--S--F--     +314

TTCCTCTACAGCAAGCTCACCGTGGACAAGAGCAGGTGGCAGCAGGGGAACGTCTTCTCA    +1002
F--L--Y--S--K--L--T--V--D--K--S--R--W--Q--Q--G--N--V--F--S--    +334

TGCTCCGTGATGCATGAGGCTCTGCACAACCACTACACGCAGAAGAGCCTCTCCCTGTCT    +1062
C--S--V--M--H--E--A--L--H--N--H--Y--T--Q--K--S--L--S--L--S--    +354

CCGGGTAAATGA
P--G--K--*
```

FIG. 8

```
ATGGGTGTACTGCTCACACAGAGGACGCTGCTCAGTCTGGTCCTTGCACTCCTGTTTCCA      -19
M---G---V---L---L---T---Q---R---T---L---L---S---L---V---L---A---L---L---F---P---  -7

AGCATGGCGAGCATGGCAATGCACGTGGCCCAGCCTGCTGTGGTACTGGCCACCAGCCGA      +42
S---M---A---S---M---A---M---H---V---A---Q---P---A---V---V---L---A---S---S---R---  +24
                                    +1

GGCATGGCTAGCTTTGTGTGTGAGTATGCATCTCCAGGCAAAGCCACTGAGGTCCGGGTG     +102
G---I---A---S---F---V---C---E---Y---A---S---P---G---K---A---T---E---V---R---V--- +34

ACAGTGCTTCGGCAGGCTGACAGCCAGGTGACTGAAGTCTGTGCGGCAACCTACATGATG     +162
T---V---L---R---Q---A---D---S---Q---V---T---E---V---C---A---A---T---Y---M---M--- +54

GGGAATGAGTTGACCTTCCTAGATGATTCCATCTGCACGGGCACCTCCAGTGGAAATCAA     +222
G---N---E---L---T---F---L---D---D---S---I---C---T---G---T---S---S---G---N---Q--- +74

GTGAACCTCACTATCCAAGGACTGAGGGCCATGGACACGGGACTCTACATCTGCAAGGTG     +282
V---N---L---T---I---Q---G---L---R---A---M---D---T---G---L---Y---I---C---K---V--- +94

GAGCTCATGTACCCACCGCCATACTACCTGGGCATAGGCAACGGAACCCAGATTTATGTA     +342
E---L---M---Y---P---P---P---Y---Y---L---G---I---G---N---G---T---Q---I---Y---V--- +114

ATTGATCCAGAACCGTGCCCAGATTCTGATCAGGAGCCAAATCTTCTGACAAAACTCAC     +402
I---D---P---E---P---C---P---D---S---D---Q---E---P---K---S---S---D---K---T---H--- +134

ACAGTCCCACCGTCCCCAGCACCTGAACTCCTGGGTGGATGTCAGTCTTCCTCTTCCCC     +462
T---S---P---P---S---P---A---P---E---L---L---G---G---S---S---V---F---L---F---P--- +154

CCAAAACCCAAGGACACCCTCATGATCTCCCGGACCCCTGAGGTCACATGCGTGGTGGTG     +522
P---K---P---K---D---T---L---M---I---S---R---T---P---E---V---T---C---V---V---V--- +174

GACGTGAGCCACGAAGACCCTGAGGTCAAGTTCAACTGGTACGTGGACGGCGTGGAGGTG     +582
D---V---S---H---E---D---P---E---V---K---F---N---W---Y---V---D---G---V---E---V--- +194

CATAATGCCAAGACAAAGCCGCGGGAGGAGCAGTACAACAGCACGTACCGGGTGGTCAGC     +642
H---N---A---K---T---K---P---R---E---E---Q---Y---N---S---T---Y---R---V---V---S--- +214

GTCCTCACCGTCCTGCACCAGGACTGGCTGAATGGCAAGGAGTACAAGTGCAAGGTCTCC     +702
V---L---T---V---L---H---Q---D---W---L---N---G---K---E---Y---K---C---K---V---S--- +234

AACAAAGCCCTCCCAGCCCCCATCGAGAAAACCATCTCCAAAGCCAAAGGGCAGCCCCGA     +762
N---K---A---L---P---A---P---I---E---K---T---I---S---K---A---K---G---Q---P---R--- +254

GAACCACAGGTGTACACCCTGCCCCCATCCCGGGATGAGCTGACCAAGAACCAGGTCAGC     +822
E---P---Q---V---Y---T---L---P---P---S---R---D---E---L---T---K---N---Q---V---S--- +274

CTGACCTGCCTGGTCAAAGGCTTCTATCCCAGCGACATCGCCGTGGAGTGGGAGAGCAAT     +882
L---T---C---L---V---K---G---F---Y---P---S---D---I---A---V---E---W---E---S---N--- +294

GGGCAGCCGGAGAACAACTACAAGACCACGCCTCCCGTGCTGGACTCCGACGGCTCCTTC     +942
G---Q---P---E---N---N---Y---K---T---T---P---P---V---L---D---S---D---G---S---F--- +314

TTCCTCTACAGCAAGCTCACCGTGGACAAGAGCAGGTGGCAGCAGGGGAACGTCTTCTCA    +1002
F---L---Y---S---K---L---T---V---D---K---S---R---W---Q---Q---G---N---V---F---S--- +334

TGCTCCGTGATGCATGAGGCTCTGCACAACCACTACACGCAGAAGAGCCTCTCCCTGTCT    +1062
C---S---V---M---H---E---A---L---H---N---H---Y---T---Q---K---S---L---S---L---S--- +354

CCGGGTAAATGA
P---G---K---*
```

FIG 9

+βME  -βME
———  ———
M 1 2 3  1 2 3 M
FIG. 10A
$M_r$ (× 10⁻³)
· 200
· 118
· 107
· 68
· 43
· 37
· 27
· 20
FIG. 10B
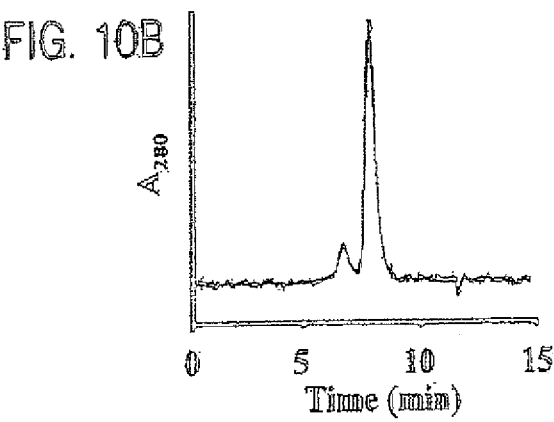
FIG. 10C
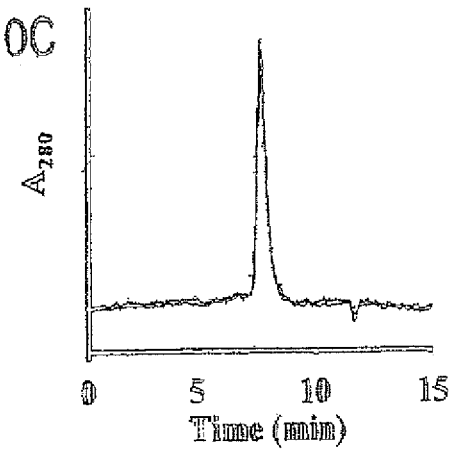

SEQUENCE LISTING

<160> NUMBER OF SEQ ID NOS: 9

<210> SEQ ID NO 1
<211> LENGTH: 41
<212> TYPE: DNA
<213> ORGANISM: Artificial Sequence
<220> FEATURE:
<223> OTHER INFORMATION: Description of Artificial Sequence:Oncostatin M
    CTLA4 (OMCTLA4) Forward Primer

<400> SEQUENCE: 1
gaggtgataa agcttcacca atgggtgtac tgctcacaca g     41

<210> SEQ ID NO 2
<211> LENGTH: 42
<212> TYPE: DNA
<213> ORGANISM: Artificial Sequence
<220> FEATURE:
<223> OTHER INFORMATION: Description of Artificial Sequence:Oncostatin M
    CTLA4 (OMCTLA4) Reverse Primer

<400> SEQUENCE: 2

-continued

```
gtggtgtatt ggtctagatc aatcagaatc tgggcacggt tc                    42
```

<210> SEQ ID NO 3
<211> LENGTH: 1152
<212> TYPE: DNA
<213> ORGANISM: Homo sapiens
<220> FEATURE:

<400> SEQUENCE: 3

```
atgggtgtac tgctcacaca gaggacgctg ctcagtctgg tccttgcact cctgtttcca    60
agcatggcga gcatggcaat gcacgtggcc cagcctgctg tggtactggc agcagccga   120
ggcatcgcta gctttgtgtg tgagtatgca tctccaggca aatatactga ggtccgggtg   180
acagtgcttc ggcaggctga cagccaggtg actgaagtct gtgcggcaac ctacatgatg   240
gggaatgagt tgaccttcct agatgattcc atctgcacgg gcacctccag tggaaatcaa   300
gtgaacctca ctatccaagg actgagggcc atggacacgg gactctacat ctgcaaggtg   360
gagctcatgt acccaccgcc atactacgag ggcataggca cggaaccca gatttatgta   420
attgatccag aaccgtgccc agattctgat caggagccca atcttctga caaaactcac   480
acatccccac cgtccccagc acctgaactc ctggggggat cgtcagtctt cctcttcccc   540
ccaaaaccca aggacaccct catgatctcc cggacccctg aggtcacatg cgtggtggtg   600
gacgtgagcc acgaagaccc tgaggtcaag ttcaactggt acgtggacgg cgtggaggtg   660
cataatgcca agacaaagcc gcgggaggag cagtacaaca gcacgtaccg tgtggtcagc   720
gtcctcaccg tcctgcacca ggactggctg aatggcaagg agtacaagtg caaggtctcc   780
aacaaagccc tcccagcccc catcgagaaa accatctcca aagccaaagg cagccccga   840
gaaccacagg tgtacaccct gcccccatcc cgggatgagc tgaccaagaa ccaggtcagc   900
ctgacctgcc tggtcaaagg cttctatccc agcgacatcg ccgtggagtg ggagagcaat   960
gggcagccgg agaacaacta caagaccacg cctcccgtgc tggactccga cggctccttc  1020
ttcctctaca gcaagctcac cgtggacaag agcaggtggc agcaggggaa cgtcttctca  1080
tgctccgtga tgcatgaggc tctgcacaac cactacacgc agaagagcct ctccctgtct  1140
ccgggtaaat ga                                                      1152
```

<210> SEQ ID NO 4
<211> LENGTH: 383
<212> TYPE: PRT
<213> ORGANISM: Artificial Sequence
<220> FEATURE:
<223> OTHER INFORMATION: Description of Artificial Sequence:L104EA29YIg

<400> SEQUENCE: 4

```
Met Gly Val Leu Leu Thr Gln Arg Thr Leu Leu Ser Leu Val Leu Ala
  1               5                  10                  15

Leu Leu Phe Pro Ser Met Ala Ser Met Ala Met His Val Ala Gln Pro
                 20                  25                  30

Ala Val Val Leu Ala Ser Ser Arg Gly Ile Ala Ser Phe Val Cys Glu
             35                  40                  45

Tyr Ala Ser Pro Gly Lys Tyr Thr Glu Val Arg Val Thr Val Leu Arg
         50                  55                  60

Gln Ala Asp Ser Gln Val Thr Glu Val Cys Ala Ala Thr Tyr Met Met
     65                  70                  75                  80

Gly Asn Glu Leu Thr Phe Leu Asp Asp Ser Ile Cys Thr Gly Thr Ser
                 85                  90                  95
```

Ser Gly Asn Gln Val Asn Leu Thr Ile Gln Gly Leu Arg Ala Met Asp
            100                 105                 110

Thr Gly Leu Tyr Ile Cys Lys Val Glu Leu Met Tyr Pro Pro Pro Tyr
            115                 120                 125

Tyr Glu Gly Ile Gly Asn Gly Thr Gln Ile Tyr Val Ile Asp Pro Glu
            130                 135                 140

Pro Cys Pro Asp Ser Asp Gln Glu Pro Lys Ser Ser Asp Lys Thr His
145                 150                 155                 160

Thr Ser Pro Pro Ser Pro Ala Pro Glu Leu Leu Gly Gly Ser Ser Val
            165                 170                 175

Phe Leu Phe Pro Pro Lys Pro Lys Asp Thr Leu Met Ile Ser Arg Thr
            180                 185                 190

Pro Glu Val Thr Cys Val Val Val Asp Val Ser His Glu Asp Pro Glu
            195                 200                 205

Val Lys Phe Asn Trp Tyr Val Asp Gly Val Glu Val His Asn Ala Lys
            210                 215                 220

Thr Lys Pro Arg Glu Glu Gln Tyr Asn Ser Thr Tyr Arg Val Val Ser
225                 230                 235                 240

Val Leu Thr Val Leu His Gln Asp Trp Leu Asn Gly Lys Glu Tyr Lys
            245                 250                 255

Cys Lys Val Ser Asn Lys Ala Leu Pro Ala Pro Ile Glu Lys Thr Ile
            260                 265                 270

Ser Lys Ala Lys Gly Gln Pro Arg Glu Pro Gln Val Tyr Thr Leu Pro
            275                 280                 285

Pro Ser Arg Asp Glu Leu Thr Lys Asn Gln Val Ser Leu Thr Cys Leu
            290                 295                 300

Val Lys Gly Phe Tyr Pro Ser Asp Ile Ala Val Glu Trp Glu Ser Asn
305                 310                 315                 320

Gly Gln Pro Glu Asn Asn Tyr Lys Thr Thr Pro Pro Val Leu Asp Ser
            325                 330                 335

Asp Gly Ser Phe Phe Leu Tyr Ser Lys Leu Thr Val Asp Lys Ser Arg
            340                 345                 350

Trp Gln Gln Gly Asn Val Phe Ser Cys Ser Val Met His Glu Ala Leu
            355                 360                 365

His Asn His Tyr Thr Gln Lys Ser Leu Ser Leu Ser Pro Gly Lys
            370                 375                 380

<210> SEQ ID NO 5
<211> LENGTH: 1152
<212> TYPE: DNA
<213> ORGANISM: Artificial Sequence
<220> FEATURE:
<223> OTHER INFORMATION: Description of Artificial Sequence:L104EIg

<400> SEQUENCE: 5
atgggtgtac tgctcacaca gaggacgctg ctcagtctgg tccttgcact cctgtttcca    60
agcatggcga gcatggcaat gcacgtggcc cagcctgctg tggtactggc cagcagccga   120
ggcatcgcta gctttgtgtg tgagtatgca tctccaggca agccactga ggtccgggtg    180 acagtgcttc ggcaggctga cagccaggtg actgaagtct gtgcggcaac ctacatgatg   240
gggaatgagt tgaccttcct agatgattcc atctgcacgg gcacctccag tggaaatcaa   300
gtgaacctca ctatccaagg actgagggc atggacacgg actctacat ctgcaaggtg    360 gagctcatgt acccaccgcc atactacgag ggcataggca cggaaccca gatttatgta    420

```
attgatccag aaccgtgccc agattctgat caggagccca atcttctga caaaactcac    480 acatccccac cgtccccagc acctgaactc ctgggggat cgtcagtctt cctcttcccc    540
ccaaaaccca aggacaccct catgatctcc cggacccctg aggtcacatg cgtggtggtg   600
gacgtgagcc acgaagaccc tgaggtcaag ttcaactggt acgtggacgg cgtggaggtg   660
cataatgcca agacaaagcc gcgggaggag cagtacaaca gcacgtaccg tgtggtcagc   720
gtcctcaccg tcctgcacca ggactggctg aatggcaagg agtacaagtg caaggtctcc   780
aacaaagccc tcccagcccc catcgagaaa accatctcca aagccaaagg gcagccccga   840
gaaccacagg tgtacaccct gcccccatcc cgggatgagc tgaccaagaa ccaggtcagc   900
ctgacctgcc tggtcaaagg cttctatccc agcgacatcg ccgtggagtg ggagagcaat   960
gggcagccgg agaacaacta caagaccacg cctcccgtgc tggactccga cggctccttc   1020
ttcctctaca gcaagctcac cgtggacaag agcaggtggc agcaggggaa cgtcttctca   1080
tgctccgtga tgcatgaggc tctgcacaac cactacacgc agaagagcct ctccctgtct   1140
ccgggtaaat ga                                                      1152
```

<210> SEQ ID NO 6
<211> LENGTH: 383
<212> TYPE: PRT
<213> ORGANISM: Artificial Sequence
<220> FEATURE:
<223> OTHER INFORMATION: Description of Artificial Sequence:L104EIg

<400> SEQUENCE: 6

```
Met Gly Val Leu Leu Thr Gln Arg Thr Leu Leu Ser Leu Val Leu Ala
 1               5                   10                  15

Leu Leu Phe Pro Ser Met Ala Ser Met Ala Met His Val Ala Gln Pro
            20                  25                  30

Ala Val Val Leu Ala Ser Ser Arg Gly Ile Ala Ser Phe Val Cys Glu
        35                  40                  45

Tyr Ala Ser Pro Gly Lys Ala Thr Glu Val Arg Val Thr Val Leu Arg
    50                  55                  60

Gln Ala Asp Ser Gln Val Thr Glu Val Cys Ala Ala Thr Tyr Met Met
65                  70                  75                  80

Gly Asn Glu Leu Thr Phe Leu Asp Asp Ser Ile Cys Thr Gly Thr Ser
                85                  90                  95

Ser Gly Asn Gln Val Asn Leu Thr Ile Gln Gly Leu Arg Ala Met Asp
            100                 105                 110

Thr Gly Leu Tyr Ile Cys Lys Val Glu Leu Met Tyr Pro Pro Pro Tyr
        115                 120                 125

Tyr Glu Gly Ile Gly Asn Gly Thr Gln Ile Tyr Val Ile Asp Pro Glu
    130                 135                 140

Pro Cys Pro Asp Ser Asp Gln Glu Pro Lys Ser Ser Asp Lys Thr His
145                 150                 155                 160

Thr Ser Pro Pro Ser Pro Ala Pro Glu Leu Leu Gly Gly Ser Ser Val
                165                 170                 175

Phe Leu Phe Pro Pro Lys Pro Lys Asp Thr Leu Met Ile Ser Arg Thr
            180                 185                 190

Pro Glu Val Thr Cys Val Val Val Asp Val Ser His Glu Asp Pro Glu
        195                 200                 205

Val Lys Phe Asn Trp Tyr Val Asp Gly Val Glu Val His Asn Ala Lys
    210                 215                 220

Thr Lys Pro Arg Glu Glu Gln Tyr Asn Ser Thr Tyr Arg Val Val Ser
```

```
                  225                 230                 235                 240

Val Leu Thr Val Leu His Gln Asp Trp Leu Asn Gly Lys Glu Tyr Lys
                            245                 250                 255

Cys Lys Val Ser Asn Lys Ala Leu Pro Ala Pro Ile Glu Lys Thr Ile
                        260                 265                 270

Ser Lys Ala Lys Gly Gln Pro Arg Glu Pro Gln Val Tyr Thr Leu Pro
                    275                 280                 285

Pro Ser Arg Asp Glu Leu Thr Lys Asn Gln Val Ser Leu Thr Cys Leu
                290                 295                 300

Val Lys Gly Phe Tyr Pro Ser Asp Ile Ala Val Glu Trp Glu Ser Asn
        305                 310                 315                 320

Gly Gln Pro Glu Asn Asn Tyr Lys Thr Thr Pro Pro Val Leu Asp Ser
                            325                 330                 335

Asp Gly Ser Phe Phe Leu Tyr Ser Lys Leu Thr Val Asp Lys Ser Arg
                        340                 345                 350

Trp Gln Gln Gly Asn Val Phe Ser Cys Ser Val Met His Glu Ala Leu
                    355                 360                 365

His Asn His Tyr Thr Gln Lys Ser Leu Ser Leu Ser Pro Gly Lys
                370                 375                 380

<210> SEQ ID NO 7
<211> LENGTH: 1152
<212> TYPE: DNA
<213> ORGANISM: Artificial Sequence
<220> FEATURE:
<223> OTHER INFORMATION: Description of Artificial Sequence:CTLA4Ig

<400> SEQUENCE: 7
atgggtgtac tgctcacaca gaggacgctg ctcagtctgg tccttgcact cctgtttcca      60
agcatggcga gcatggcaat gcacgtggcc cagcctgctg tggtactggc cagcagccga     120
ggcatcgcta gctttgtgtg tgagtatgca tctccaggca agccactga ggtccgggtg      180 acagtgcttc ggcaggctga cagccaggtg actgaagtct gtgcggcaac ctacatgatg     240
gggaatgagt tgaccttcct agatgattcc atctgcacgg gcacctccag tggaaatcaa     300
gtgaacctca ctatccaagg actgagggcc atggacacgg gactctacat ctgcaaggtg     360
gagctcatgt acccaccgcc atactacctg ggcataggca acggaaccca gatttatgta     420
attgatccag aaccgtgccc agattctgat caggagccca atcttctga caaaactcac      480 acatccccac cgtccccagc acctgaactc ctgggtggat cgtcagtctt cctcttcccc     540
ccaaaaccca aggacaccct catgatctcc cggacccctg aggtcacatg cgtggtggtg     600
gacgtgagcc acgaagaccc tgaggtcaag ttcaactggt acgtggacgg cgtggaggtg     660
cataatgcca agacaaagcc gcgggaggag cagtacaaca gcacgtaccg ggtggtcagc     720
gtcctcaccg tcctgcacca ggactggctg aatggcaagg agtacaagtg caaggtctcc     780
aacaaagccc tcccagcccc catcgagaaa accatctcca aagccaaagg cagccccga    840 gaaccacagg tgtacaccct gcccccatcc cgggatgagc tgaccaagaa ccaggtcagc     900
ctgacctgcc tggtcaaagg cttctatccc agcgacatcg ccgtggagtg ggagagcaat     960
gggcagccgg agaacaacta caagaccacg cctcccgtgc tggactccga cggctccttc    1020
ttcctctaca gcaagctcac cgtggacaag agcaggtggc agcagggaa cgtcttctca     1080 tgctccgtga tgcatgaggc tctgcacaac cactacacgc agaagagcct ctccctgtct    1140
ccgggtaaat ga                                                        1152
```

```
<210> SEQ ID NO 8
<211> LENGTH: 383
<212> TYPE: PRT
<213> ORGANISM: Artificial Sequence
<220> FEATURE:
<223> OTHER INFORMATION: Description of Artificial Sequence:CTLA4Ig

<400> SEQUENCE: 8

Met Gly Val Leu Leu Thr Gln Arg Thr Leu Leu Ser Leu Val Leu Ala
 1               5                  10                  15

Leu Leu Phe Pro Ser Met Ala Ser Met Ala Met His Val Ala Gln Pro
             20                  25                  30

Ala Val Val Leu Ala Ser Ser Arg Gly Ile Ala Ser Phe Val Cys Glu
         35                  40                  45

Tyr Ala Ser Pro Gly Lys Ala Thr Glu Val Arg Val Thr Val Leu Arg
     50                  55                  60

Gln Ala Asp Ser Gln Val Thr Glu Val Cys Ala Ala Thr Tyr Met Met
 65                  70                  75                  80

Gly Asn Glu Leu Thr Phe Leu Asp Asp Ser Ile Cys Thr Gly Thr Ser
                 85                  90                  95

Ser Gly Asn Gln Val Asn Leu Thr Ile Gln Gly Leu Arg Ala Met Asp
            100                 105                 110

Thr Gly Leu Tyr Ile Cys Lys Val Glu Leu Met Tyr Pro Pro Pro Tyr
        115                 120                 125

Tyr Leu Gly Ile Gly Asn Gly Thr Gln Ile Tyr Val Ile Asp Pro Glu
    130                 135                 140

Pro Cys Pro Asp Ser Asp Gln Glu Pro Lys Ser Ser Asp Lys Thr His
145                 150                 155                 160

Thr Ser Pro Pro Ser Pro Ala Pro Glu Leu Leu Gly Gly Ser Ser Val
                165                 170                 175

Phe Leu Phe Pro Pro Lys Pro Lys Asp Thr Leu Met Ile Ser Arg Thr
            180                 185                 190

Pro Glu Val Thr Cys Val Val Val Asp Val Ser His Glu Asp Pro Glu
        195                 200                 205

Val Lys Phe Asn Trp Tyr Val Asp Gly Val Glu Val His Asn Ala Lys
    210                 215                 220

Thr Lys Pro Arg Glu Glu Gln Tyr Asn Ser Thr Tyr Arg Val Val Ser
225                 230                 235                 240

Val Leu Thr Val Leu His Gln Asp Trp Leu Asn Gly Lys Glu Tyr Lys
                245                 250                 255

Cys Lys Val Ser Asn Lys Ala Leu Pro Ala Pro Ile Glu Lys Thr Ile
            260                 265                 270

Ser Lys Ala Lys Gly Gln Pro Arg Glu Pro Gln Val Tyr Thr Leu Pro
        275                 280                 285

Pro Ser Arg Asp Glu Leu Thr Lys Asn Gln Val Ser Leu Thr Cys Leu
    290                 295                 300

Val Lys Gly Phe Tyr Pro Ser Asp Ile Ala Val Glu Trp Glu Ser Asn
305                 310                 315                 320

Gly Gln Pro Glu Asn Asn Tyr Lys Thr Thr Pro Pro Val Leu Asp Ser
                325                 330                 335

Asp Gly Ser Phe Phe Leu Tyr Ser Lys Leu Thr Val Asp Lys Ser Arg
            340                 345                 350

Trp Gln Gln Gly Asn Val Phe Ser Cys Ser Val Met His Glu Ala Leu
        355                 360                 365
```

```
His Asn His Tyr Thr Gln Lys Ser Leu Ser Leu Ser Pro Gly Lys
    370                 375                 380

<210> SEQ ID NO 9
<211> LENGTH: 6
<212> TYPE: PRT
<213> ORGANISM: Homo sapiens
<220> FEATURE:

<400> SEQUENCE: 9

Met Tyr Pro Pro Pro Tyr
  1               5
```

US 9,758,565 B2

METHODS OF TREATMENT USING CTLA4 MUTANT MOLECULES

This application is a continuation of U.S. application Ser. No. 13/277,425, filed Oct. 20, 2011, now allowed, which is a divisional of U.S. application Ser. No. 12/694,327, filed Jan. 27, 2010, now abandoned, which is a divisional of U.S. application Ser. No. 11/725,762, filed Mar. 20, 2007, issued as U.S. Pat. No. 7,700,556, which is a divisional of U.S. application Ser. No. 10/980,742, filed Nov. 3, 2004, issued as U.S. Pat. No. 7,439,230, which is a divisional of U.S. application Ser. No. 09/865,321, filed May 23, 2001, issued as U.S. Pat. No. 7,094,874, which claims priority to U.S. Ser. No. 09/579,927, filed May 26, 2000, now abandoned; 60/287,576, filed May 26, 2000, now abandoned and 60/214,065 filed Jun. 26, 2000, now abandoned. The contents of all of the foregoing applications in their entireties are incorporated by reference into the present application.

Throughout this application various publications are referenced. The disclosures of these publications in their entireties are hereby incorporated by reference into this application in order to more fully describe the state of the art to which this invention pertains.

FIELD OF THE INVENTION

The present invention relates to the field of soluble CTLA4 molecules that are mutated from wild type CTLA4 to retain the ability to bind CD80 and/or CD86.

BACKGROUND OF THE INVENTION

Antigen-nonspecific intercellular interactions between T-lymphocytes and antigen-presenting cells (APCs) generate T cell costimulatory signals that generate T cell responses to antigen (Jenkins and Johnson (1993) Curr. Opin. Immunol. 5:361-367). Costimulatory signals determine the magnitude of a T cell response to antigen, and whether this response activates or inactivates subsequent responses to antigen (Mueller et al. (1989) Annu. Rev. Immunol. 7:445-480).

T cell activation in the absence of costimulation results in an aborted or anergic T cell response (Schwartz, R. H. (1992) Cell 71:1065-1068). One key costimulatory signal is provided by interaction of the T cell surface receptor CD28 with B7 related molecules on antigen presenting cells (e.g., also known as B7-1 and B7-2, or CD80 and CD86, respectively) (P. Linsley and J. Ledbetter (1993) Annu. Rev. Immunol. 11:191-212).

The molecule now known as CD80 (B7-1) was originally described as a human B cell-associated activation antigen (Yokochi, T. et al. (1981). Immunol. 128:823-827; Freeman, G. J. et al. (1989) J. Immunol. 143:2714-2722), and subsequently identified as a counterreceptor for the related T cell molecules CD28 and CTLA4 (Linsley, P., et al. (1990) Proc. Natl. Acad. Sci. USA 87:5031-5035; Linsley, P. S. et al. (1991a) J. Exp. Med. 173:721-730; Linsley, P. S. et al. (1991b) J. Exp. Med. 174:561-570).

More recently, another counterreceptor for CTLA4 was identified on antigen presenting cells (Azuma, N. et al. (1993) Nature 366:76-79; Freeman (1993a) Science 262:909-911; Freeman, G. J. et al. (1993b) J. Exp. Med. 178:2185-2192; Hathcock, K. L. S., et al. (1994) J. Exp. Med. 180:631-640; Lenschow, D. J. et al., (1993) Proc. Natl. Acad. Sci. USA 90:11054-11058; Ravi-Wolf, Z., et al. (1993) Proc. Natl. Acad. Sci. USA 90:11182-11186; Wu, Y. et al. (1993) J. Exp. Med. 178:1789-1793). This molecule, now known as CD86 (Caux, C., et al. (1994) J. Exp. Med. 180:1841-1848), but also called B7-0 (Azuma et al., (1993), supra) or B7-2 (Freeman et al., (1993a), supra), shares about 25% sequence identity with CD80 in its extracellular region (Azuma et al., (1993), supra; Freeman et al, (1993a), supra, (1993b), supra). CD86-transfected cells trigger CD28-mediated T cell responses (Azuma et al., (1993), supra; Freeman et al., (1993a), (1993b), supra).

Comparisons of expression of CD80 and CD86 have been the subject of several studies (Azuma et al. (1993), supra; Hathcock et al., (1994) supra; Larsen, C. P., et al. (1994) J. Immunol. 152:5208-5219; Stack, R. M., et al., (1994). Immunol. 152:5723-5733). Current data indicate that expression of CD80 and CD86 are regulated differently, and suggest that CD86 expression tends to precede CD80 expression during an immune response.

Soluble forms of CD28 and CTLA4 have been constructed by fusing variable (v)-like extracellular domains of CD28 and CTLA4 to immunoglobulin (Ig) constant domains resulting in CD28Ig and CTLA4Ig. CTLA4Ig binds both CD80 positive and CD86 positive cells more strongly than CD28Ig (Linsley, P. et al. (1994) Immunity 1:793-80). Many T cell-dependent immune responses are blocked by CTLA4Ig both in vitro and in vivo. (Linsley, et al, (1991b), supra; Linsley, P. S. et al., (1992a) Science 257:792-795; Linsley, P. S. et al., (1992b) J. Exp. Med. 176:1595-1604; Lenschow, D. J. et al. (1992), Science 257:789-792; Tan, P. et al., (1992) J. Exp. Med. 177:165-173; Turka, L. A., (1992) Proc. Natl. Acad. Sci. USA 89:11102-11105).

Peach et al., (J. Exp. Med. (1994) 180:2049-2058) identified regions in the CTLA4 extracellular domain which are important for strong binding to CD80. Specifically, a hexapeptide motif (MYPPPY, SEQ ID NO:9) in the complementarity determining region 3 (CDR3)-like region was identified as fully conserved in all CD28 and CTLA4 family members. Alanine scanning mutagenesis through the MYPPPY motif (SEQ ID NO:9) in CTLA4 and at selected residues in CD28Ig reduced or abolished binding to CD80.

Chimeric molecules interchanging homologous regions of CTLA4 and CD28 were also constructed. Molecules HS4, HS4-A and HS4-B were constructed by grafting CDR3-like regions of CTLA4, which also included a portion carboxy terminally, extended to include certain nonconserved amino acid residues onto CD28Ig. These homologue mutants showed higher binding avidity to CD80 than did CD28Ig.

In another group of chimeric homologue mutants, the CDR1-like region of CTLA4, which is not conserved in CD28 and is predicted to be spatially adjacent to the CDR3-like region, was grafted, into HS4 and HS4-A. These chimeric homologue mutant molecules (designated HS7 and HS8) demonstrated even greater binding avidity for CD80 than did CD28Ig.

Chimeric homologue mutant molecules were also made by grafting into HS7 and HS8 the CDR2-like region of CTLA4, but this combination did not further improve the binding avidity for CD80. Thus, the MYPPPY motif of CTLA4 and CD28 was determined to be critical for binding to CD80, but certain non-conserved amino acid residues in the CDR1- and CDR3-like regions of CTLA4 were also responsible for increased binding avidity of CTLA4 with CD80.

CTLA4Ig was shown to effectively block CD80-associated T cell co-stimulation but was not as effective at blocking CD86-associated responses. Soluble CTLA4 mutant molecules, especially those having a higher avidity for CD86 than wild type CTLA4, were constructed as possibly better able to block the priming of antigen specific activated cells than CTLA4Ig.

There remains a need for improved CTLA4 molecules to provide better pharmaceutical compositions for immune suppression and cancer treatment than previously known soluble forms of CTLA4.

SUMMARY OF INVENTION

Accordingly, the invention provides soluble CTLA4 mutant molecules that bind CD80 and/or CD86. Mutant molecules of the invention include those that can recognize and bind either of CD80, CD86, or both. In some embodiments, mutant molecules bind CD80 and/or CD86 with greater avidity than CTLA4.

One example of a CTLA4 mutant molecule is L104EA29YIg (FIG. 7), as described herein. Another example of a CTLA4 mutant molecule is L104EIg (FIG. 8), as described herein. L104EA29YIg and L104EIg bind CD80 and CD86 more avidly than CTLA4Ig.

BRIEF DESCRIPTION OF THE FIGURES

FIG. 7 depicts a nucleotide (SEQ ID NO: 3) and amino acid sequence (SEQ ID NO:4) of a CTLA4 mutant molecule (L104EA29YIg) comprising a signal peptide; a mutated extracellular domain of CTLA4 starting at methionine at position +1 and ending at aspartic acid at position +124, or starting at alanine at position −1 and ending at aspartic acid at position +124; and an Ig region as described in Example 1, infra.

FIG. 8 depicts a nucleotide (SEQ ID NO:5) and amino acid sequence (SEQ ID NO:6) of a CTLA4 mutant molecule (L104EIg) comprising a signal peptide; a mutated extracellular domain of CTLA4 starting at methionine at position +1 and ending at aspartic acid at position +124, or starting at alanine at position −1 and ending at aspartic acid at position +124; and an Ig region as described in Example 1, infra.

FIG. 9 depicts a nucleotide (SEQ ID NO:7) and amino acid sequence (SEQ ID NO:8) of a CTLA4Ig having a signal peptide; a wild type amino acid sequence of the extracellular domain of CTLA4 starting at methionine at position +1 to aspartic acid at position +124, or starting at alanine at position −1 to aspartic acid at position +124; and an Ig region.

FIGS. 10A-C are an SDS gel (FIG. 10A) for CTLA4Ig (lane 1), L104EIg (lane 2), and L104EA29YIg (lane 3A); and size exclusion chromatographs of CTLA4Ig (FIG. 10B) and L104EA29YIg (FIG. 10C).

DETAILED DESCRIPTION OF THE INVENTION

Definitions

Figure 1:
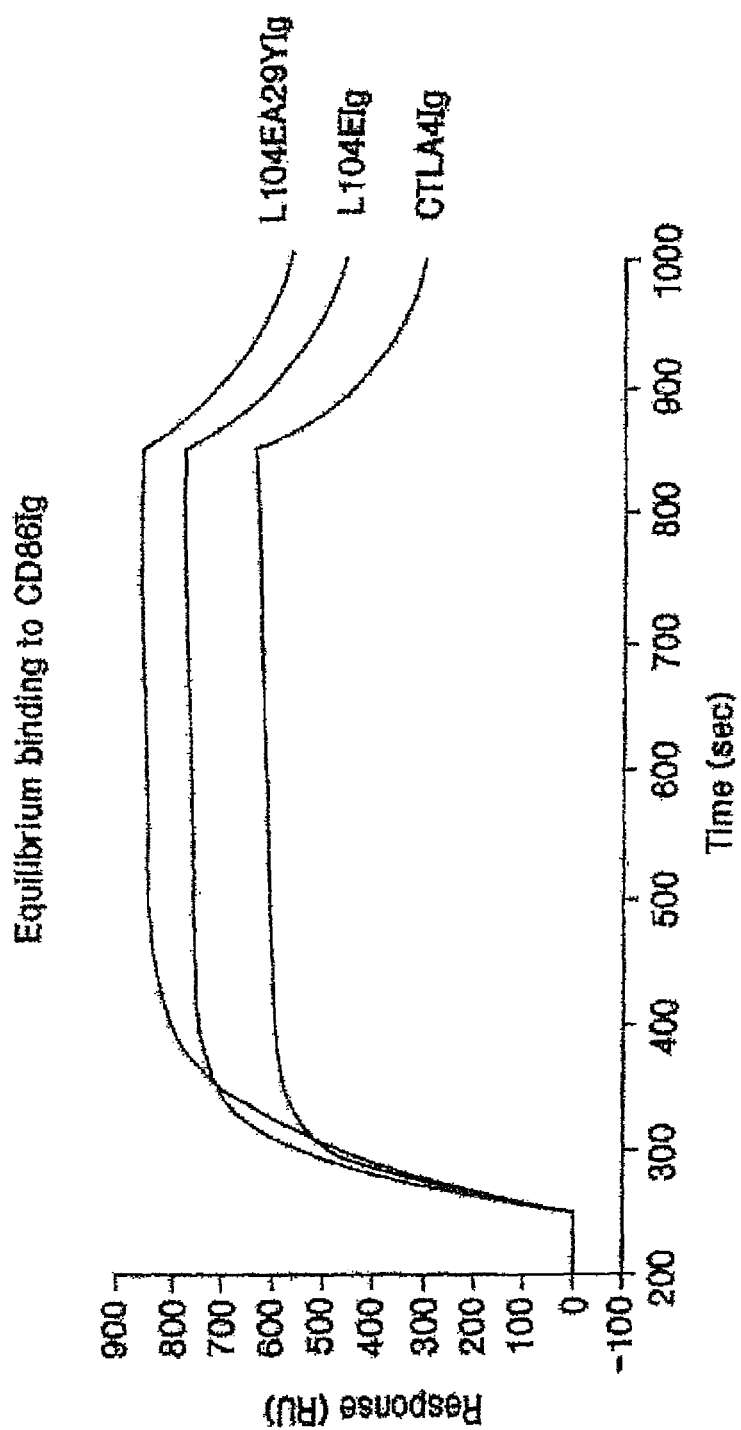
FIG. 1 shows the equilibrium binding analysis of L104EA29YIg, L104EIg, and wild-type CTLA4Ig to CD86Ig.
Figure 2A:
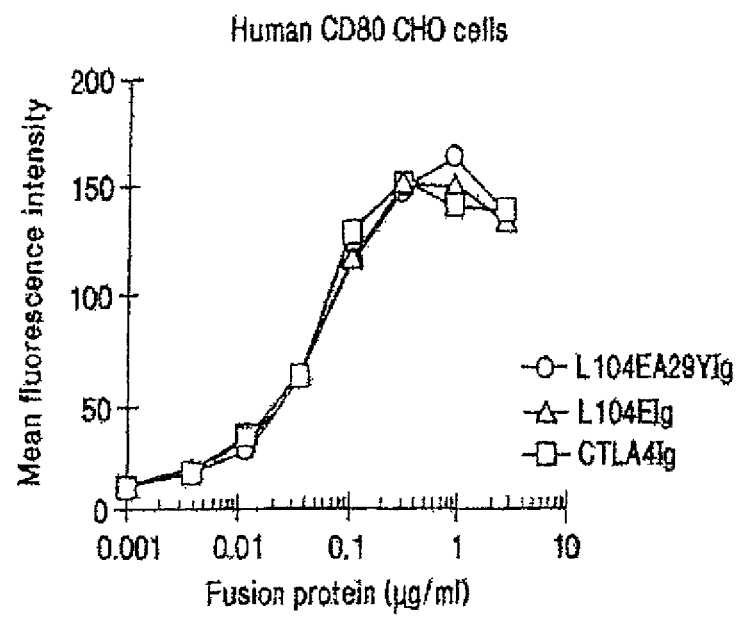
FIGS. 2A & 2B illustrate data from FACS assays showing binding of L104EA29YIg, L104EIg, and CTLA4Ig to human CD80- or CD86-transfected CHO cells as described in Example 2, infra.
Figure 2B:
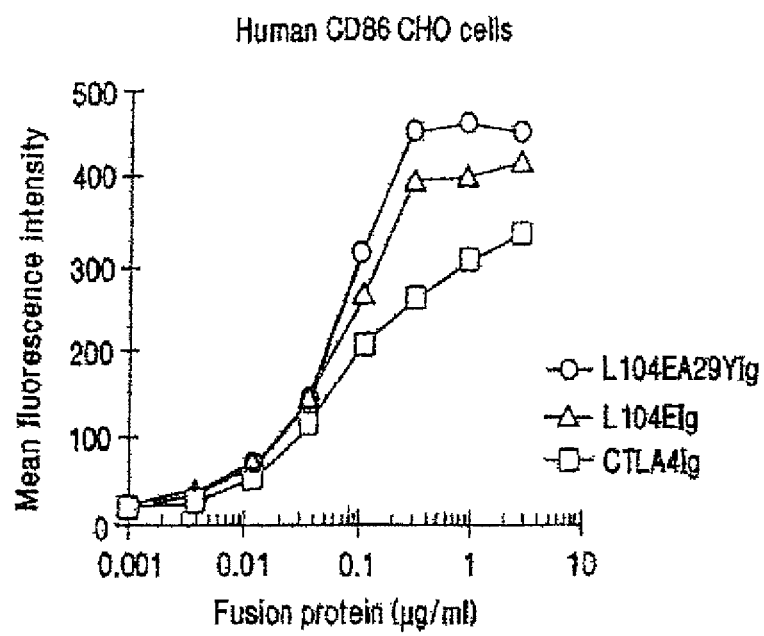
Figure 3A:
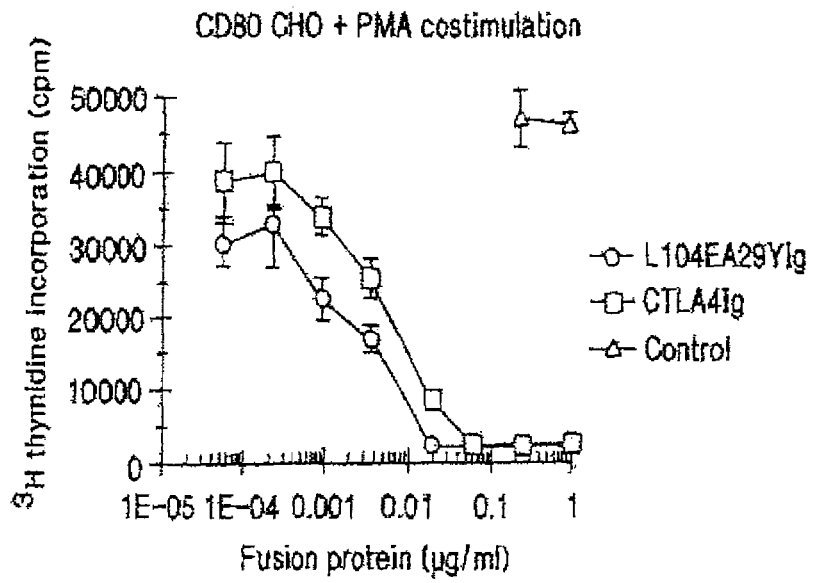
FIGS. 3A & 3B depicts inhibition of proliferation of CD80-positive and CD86-positive CHO cells as described in Example 2, infra.
Figure 3B:
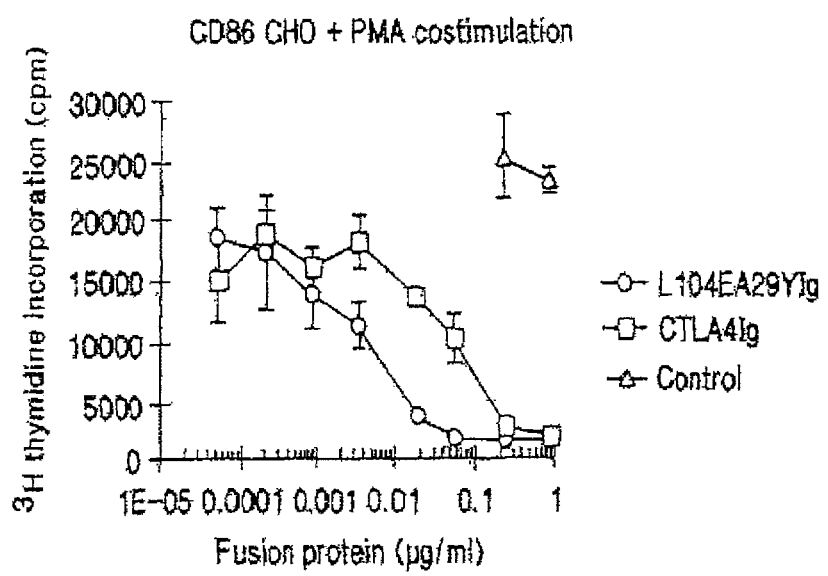
Figure 4A:
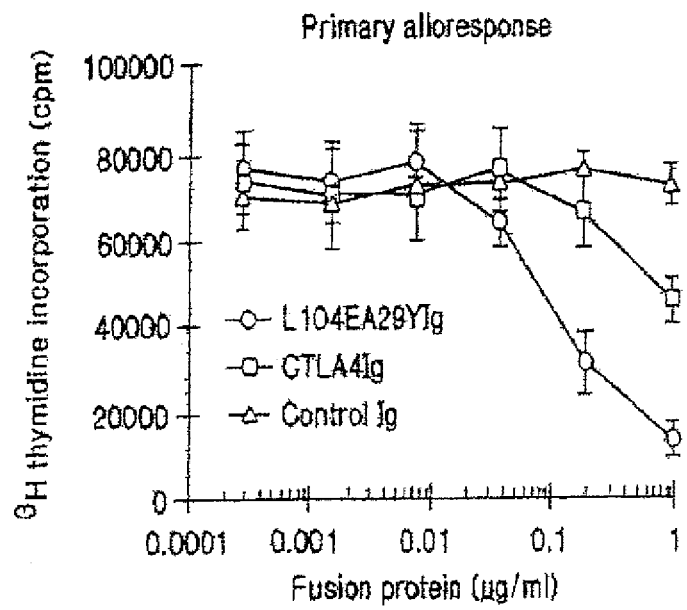
FIGS. 4A & 4B shows that L104EA29YIg is more effective than CTLA4Ig at inhibiting proliferation of primary and secondary allostimulated T cells as described in Example 2, infra.
Figure 4B:
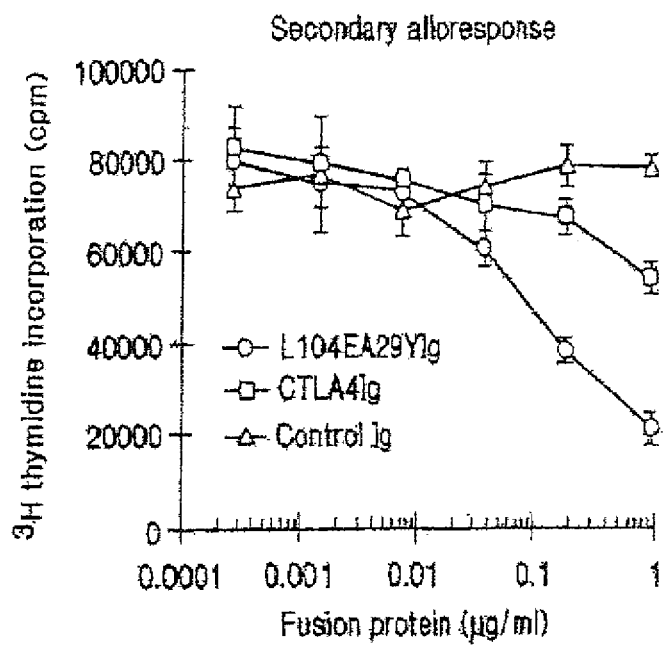
Figure 5A:
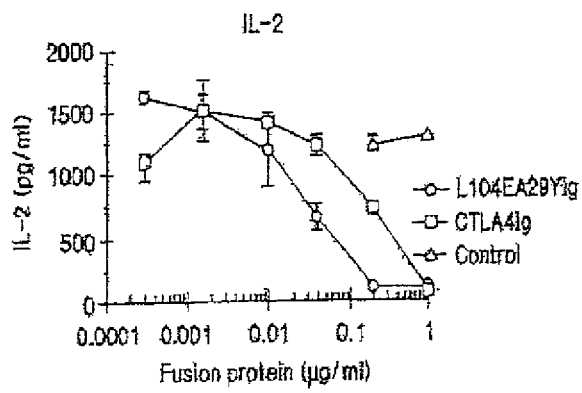
FIGS. 5A-C illustrate that L104EA29YIg is more effective than CTLA4Ig at inhibiting IL-2 (FIG. 5A), IL-4 (FIG. 5B), and γ-interferon (FIG. 5C) cytokine production of allostimulated human T cells as described in Example 2, infra.
Figure 5B:
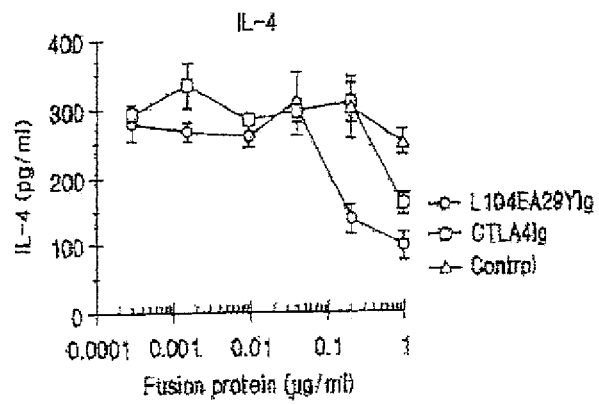
Figure 5C:
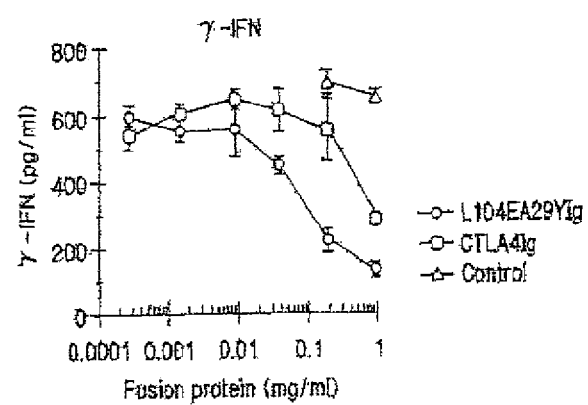
Figure 6:
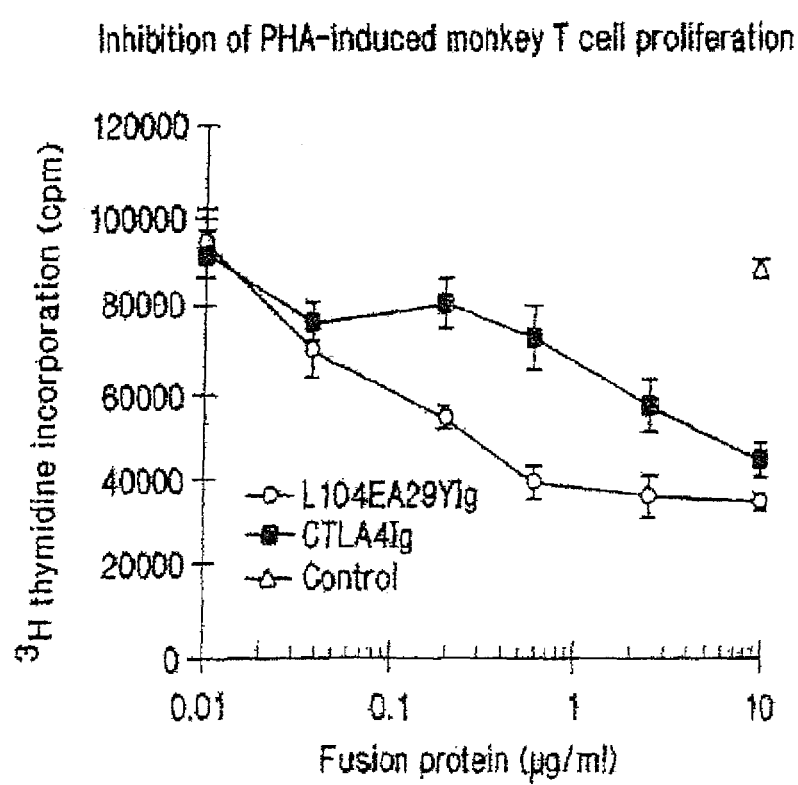
FIG. 6 demonstrates that L104EA29YIg is more effective than CTLA4Ig at inhibiting proliferation of phytohemaglutinin-(PHA) stimulated monkey T cells as described in Example 2, infra.

As used in this application, the following words or phrases have the meanings specified.

As used herein "wild type CTLA4" has the amino acid sequence of naturally occurring, full length CTLA4 (U.S. Pat. Nos. 5,434,131, 5,844,095, 5,851,795), or the extracellular domain thereof, which binds CD80 and/or CD86, and/or interferes with CD80 and/or CD86 from binding their ligands. In particular embodiments, the extracellular domain of wild type CTLA4 begins with methionine at position +1 and ends at aspartic acid at position +124, or the extracellular domain of wild type CTLA4 begins with alanine at position −1 and ends at aspartic acid at position +124. Wild type CTLA4 is a cell surface protein, having an N-terminal extracellular domain, a transmembrane domain, and a C-terminal cytoplasmic domain. The extracellular domain binds to target antigens, such as CD80 and CD86. In a cell, the naturally occurring, wild type CTLA4 protein is translated as an immature polypeptide, which includes a signal peptide at the N-terminal end. The immature polypeptide undergoes post-translational processing, which includes cleavage and removal of the signal peptide to generate a CTLA4 cleavage product having a newly generated N-terminal end that differs from the N-terminal end in the immature form. One skilled in the art will appreciate that additional post-translational processing may occur, which removes one or more of the amino acids from the newly generated N-terminal end of the CTLA4 cleavage product. The mature form of the CTLA4 molecule includes the extracellular domain of CTLA4, or any portion thereof, which binds to CD80 and/or CD86.

"CTLA4Ig" is a soluble fusion protein comprising an extracellular domain of wild type CTLA4, or a portion thereof that binds CD80 and/or CD86, joined to an Ig tail. A particular embodiment comprises the extracellular domain of wild type CTLA4 starting at methionine at position +1 and ending at aspartic acid at position +124; or starting at alanine at position −1 to aspartic acid at position +124; a junction amino acid residue glutamine at position +125; and an immunoglobulin portion encompassing glutamic acid at position +126 through lysine at position +357 (FIG. 9).

As used herein, a "fusion protein" is defined as one or more amino acid sequences joined together using methods well known in the art and as described in U.S. Pat. No. 5,434,131 or 5,637,481. The joined amino acid sequences thereby form one fusion protein.

As used herein a "CTLA4 mutant molecule" is a molecule that can be full length CTLA4 or portions thereof (derivatives or fragments) that have a mutation or multiple mutations in CTLA4 (preferably in the extracellular domain of CTLA4) so that it is similar but no longer identical to the wild type CTLA4 molecule. CTLA4 mutant molecules bind either CD80 or CD86, or both. Mutant CTLA4 molecules may include a biologically or chemically active non-CTLA4 molecule therein or attached thereto. The mutant molecules may be soluble (i.e., circulating) or bound to a surface. CTLA4 mutant molecules can include the entire extracellular domain of CTLA4 or portions thereof, e.g., fragments or derivatives. CTLA4 mutant molecules can be made synthetically or recombinantly.

As used herein, the term "mutation" is a change in the nucleotide or amino acid sequence of a wild-type polypeptide. In this case, it is a change in the wild type CTLA4 extracellular domain. The change can be an amino acid change which includes substitutions, deletions, additions, or truncations. A mutant molecule can have one or more mutations. Mutations in a nucleotide sequence may or may not result in a mutation in the amino acid sequence as is well understood in the art. In that regard, certain nucleotide codons encode the same amino acid. Examples include nucleotide codons CGU, CGG, CGC, and CGA encoding the amino acid, arginine (R); or codons GAU, and GAC encoding the amino acid, aspartic acid (D). Thus, a protein can be encoded by one or more nucleic acid molecules that differ in their specific nucleotide sequence, but still encode protein molecules having identical sequences. The amino acid coding sequence is as follows:

| Amino Acid | Symbol | One Letter Symbol | Codons |
|---|---|---|---|
| Alanine | Ala | A | GCU, GCC, GCA, GCG |
| Cysteine | Cys | C | UGU, UGC |
| Aspartic Acid | Asp | D | GAU, GAC |
| Glutamic Acid | Glu | E | GAA, GAG |
| Phenylalanine | Phe | F | UUU, UUC |
| Glycine | Gly | G | GGU, GGC, GGA, GGG |
| Histidine | His | H | CAU, CAC |
| Isoleucine | Ile | I | AUU, AUC, AUA |
| Lysine | Lys | K | AAA, AAG |
| Leucine | Leu | L | UUA, UUG, CUU, CUC, CUA, CUG |
| Methionine | Met | M | AUG |
| Asparagine | Asn | N | AAU, AAC |
| Proline | Pro | P | CCU, CCC, CCA, CCG |
| Glutamine | Gln | Q | CAA, CAG |
| Arginine | Arg | R | CGU, CGC, CGA, CGG, AGA, AGG |
| Serine | Ser | S | UCU, UCC, UCA, UCG, AGU, AGC |
| Threonine | Thr | T | ACU, ACC, ACA, ACG |
| Valine | Val | V | GUU, GUC, GUA, GUG |
| Tryptophan | Trp | W | UGG |
| Tyrosine | Tyr | Y | UAU, UAC |

As used herein "the extracellular domain of CTLA4" is a portion of CTLA4 that recognizes and binds CD80 and/or CD86. For example, an extracellular domain of CTLA4 comprises methionine at position +1 to aspartic acid at position +124 (FIG. 9). Alternatively, an extracellular domain of CTLA4 comprises alanine at position −1 to aspartic acid at position +124 (FIG. 9). The extracellular domain includes fragments or derivatives of CTLA4 that bind CD80 and/or CD86.

As used herein a "non-CTLA4 protein sequence" or "non-CTLA4 molecule" is defined as any molecule that does not bind CD80 and/or CD86 and does not interfere with the binding of CTLA4 to its target. An example includes, but is not limited to, an immunoglobulin (Ig) constant region or portion thereof. Preferably, the Ig constant region is a human or monkey Ig constant region, e.g., human C(gamma)1, including the hinge, CH2 and CH3 regions. The Ig constant region can be mutated to reduce its effector functions (U.S. Pat. Nos. 5,637,481; and 6,132,992).

As used herein a "fragment of a CTLA4 mutant molecule" is a part of a CTLA4 mutant molecule, preferably the extracellular domain of CTLA4 or a part thereof, that recognizes and binds its target, e.g., CD80 and/or CD86.

As used herein a "derivative of a CTLA4 mutant molecule" is a molecule that shares at least 70% sequence similarity with and functions like the extracellular domain of CTLA4, i.e., it recognizes and binds CD80 and/or CD86.

As used herein, a "portion of a CTLA4 molecule" includes fragments and derivatives of a CTLA4 molecule that binds CD80 and/or CD86.

In order that the invention herein described may be more fully understood, the following description is set forth.

Compositions of the Invention

The present invention provides soluble CTLA4 mutant molecules that recognize and bind CD80 and/or CD86. In some embodiments, the soluble CTLA4 mutants have a higher avidity to CD80 and/or CD86 than CTLA4Ig.

Examples of CTLA4 mutant molecules include L104EA29YIg (FIG. 7). The amino acid sequence of L104EA29YIg can begin at alanine at amino acid position −1 and end at lysine at amino acid position +357. Alternatively, the amino acid sequence of L104EA29YIg can begin at methionine at amino acid position +1 and end at lysine at amino acid position +357. The CTLA4 portion of L104EA29YIg encompasses methionine at amino acid position +1 through aspartic acid at amino acid position +124. L104EA29YIg comprises a junction amino acid residue glutamine at position +125 and an immunoglobulin portion encompassing glutamic acid at position +126 through lysine at position +357 (FIG. 7). L104EA29YIg binds approximately 2-fold more avidly than wild type CTLA4Ig (hereinafter referred to as CTLA4Ig) to CD80 and approximately 4-fold more avidly to CD86. This stronger binding results in L104EA29YIg being more affective than CTLA4Ig at blocking immune responses.

CTLA4 mutant molecules comprise at least the extracellular domain of CTLA4, or portions thereof that bind CD80 and/or CD86. The extracellular portion of a CTLA4 mutant molecule comprises an amino acid sequence starting with methionine at position +1 through aspartic acid at position +124 (FIG. 7 or 8). Alternatively, the extracellular portion of the CTLA4 can comprise an amino acid sequence starting with alanine at position −1 through aspartic acid at position +124 (FIG. 7 or 8).

In one embodiment, the soluble CTLA4 mutant molecule is a fusion protein comprising the extracellular domain of CTLA4 having one or more mutations in a region of an amino acid sequence beginning with serine at +25 and ending with arginine at +33 (S25-R33). For example, the alanine at position +29 of wild type CTLA4 can be substituted with tyrosine (codons: UAU, UAC). Alternatively, alanine can be substituted with leucine (codons: UUA, UUG, CUU, CUC, CUA, CUG), phenylalanine (codons: UUU, UUC), tryptophan (codon: UGG), or threonine (codons: ACU, ACC, ACA, ACG). As persons skilled in the art will readily understand, the uracil (U) nucleotide of the RNA sequence corresponds to the thymine (T) nucleotide of the DNA sequence.

In another embodiment, the soluble CTLA4 mutant molecule is a fusion protein comprising the extracellular domain of CTLA4 having one or more mutations in or near a region of an amino acid sequence beginning with methionine at +97 and ending with glycine at +107 (M97-G107). For example, leucine at position +104 of wild type CTLA4 can be substituted with glutamic acid (codons: GAA, GAG). A CTLA4 mutant molecule having this substitution is referred to herein as L104EIg (FIG. 8).

Figure 7:
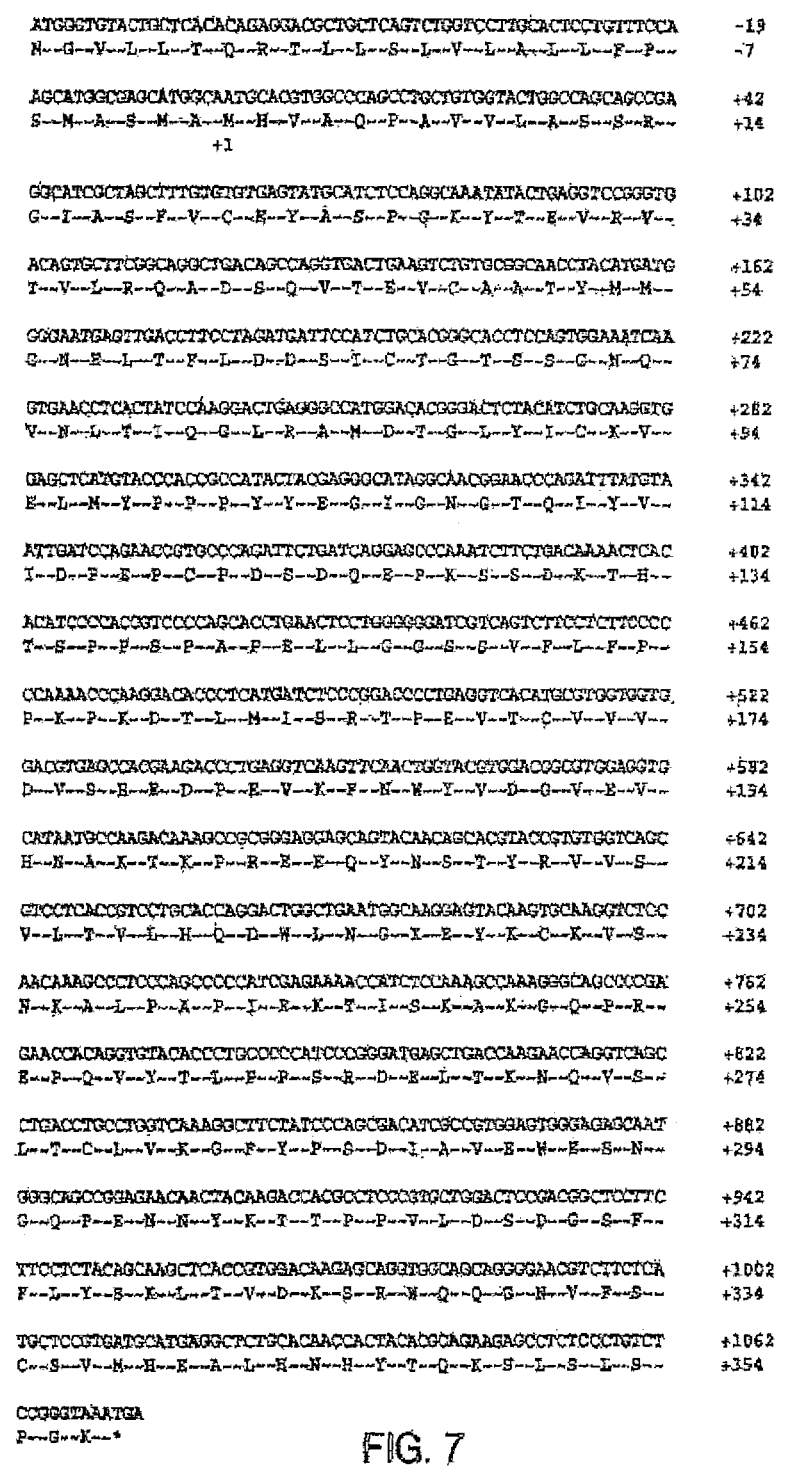

In yet another embodiment, the soluble CTLA4 mutant molecule is a fusion protein comprising the extracellular domain of CTLA4 having one or more mutations in the S25-R33 and M97-G107 regions. For example, in one embodiment, a CTLA4 mutant molecule comprises tyrosine at position +29 instead of alanine; and glutamic acid at position +104 instead of leucine. A CTLA4 mutant molecule having these substitutions is referred to herein as L104EA29YIg (FIG. 7). The nucleic acid molecule that encodes L104EA29YIg is contained in pD16 L104EA29YIg and was deposited on Jun. 20, 2000 with the American Type Culture Collection (ATCC), 10801 University Blvd., Manassas, Va. 20110-2209 (ATCC No. PTA-2104). The pD16 L104EA29YIg vector is a derivative of the pcDNA3 vector (INVITROGEN).

The invention further provides a soluble CTLA4 mutant molecule comprising an extracellular domain of a CTLA4 mutant as shown in FIG. 7 or 8, or portion(s) thereof, and a moiety that alters the solubility, affinity and/or valency of the CTLA4 mutant molecule.

In accordance with a practice of the invention, the moiety can be an immunoglobulin constant region or portion thereof. For in vive use, it is preferred that the immunoglobulin constant region does not elicit a detrimental immune response in the subject. For example, in clinical protocols, it may be preferred that mutant molecules include human or monkey immunoglobulin constant regions. One example of a suitable immunoglobulin region is human C(gamma)1, comprising the hinge, CH2, and CH3 regions. Other isotypes are possible. Further, other immunoglobulin constant regions are possible (preferably other weakly or non-immunogenic immunoglobulin constant regions).

Other moieties include polypeptide tags. Examples of suitable tags include but are not limited to the p97 molecule, env gp120 molecule, E7 molecule, and ova molecule (Dash, B., et al. (1994) *J. Gen. Virol.* 75:1389-97; Ikeda, T., et al. (1994) *Gene* 138:193-6; Falk, K., et al. (1993) *Cell. Immunol.* 150:447-52; Fujisaka, K. et al. (1994) *Virology* 204: 789-93). Other molecules for use as tags are possible (Gerard, C. et al. (1994) *Neuroscience* 62:721-739; Byrn, R. et al. *J. Virol.* (1989) 63:4370-4375; Smith, D. et al., (1987) *Science* 238:1704-1707; Lasky, L., (1996) *Science* 233:209-212).

The invention further provides soluble mutant CTLA4Ig fusion proteins preferentially more reactive with the CD80 and/or CD86 antigen compared to wild type CTLA4. One example is L104EA29YIg as shown in FIG. 7.

In another embodiment, the soluble CTLA4 mutant molecule includes a junction amino acid residue, which is located between the CTLA4 portion and the immunoglobulin portion. The junction amino acid can be any amino acid, including glutamine. The junction amino acid can be introduced by molecular or chemical synthesis methods known in the art.

In another embodiment, the soluble CTLA4 mutant molecule includes the immunoglobulin portion (e.g., hinge, CH2 and CH3 domains), where any or all of the cysteine residues, within the hinge domain of the immunoglobulin portion are substituted with serine, for example, the cysteines at positions +130, +136, or +139 (FIG. 7 or 8). The mutant molecule may also include the proline at position +148 substituted with a serine, as shown in FIG. 7 or 8.

The soluble CTLA4 mutant molecule can include a signal peptide sequence linked to the N-terminal end of the extracellular domain of the CTLA4 portion of the mutant molecule. The signal peptide can be any sequence that will permit secretion of the mutant molecule, including the signal peptide from oncostatin M (Malik, et al., (1989) *Molec. Cell. Biol.* 9: 2847-2853), or CD5 (Jones, N. H. et al., (1986) *Nature* 323:346-349), or the signal peptide from any extracellular protein.

The mutant molecule can include the oncostatin M signal peptide linked at the N-terminal end of the extracellular domain of CTLA4, and the human immunoglobulin molecule (e.g., hinge, CH2 and CH3) linked to the C-terminal end of the extracellular domain of CTLA4. This molecule includes the oncostatin M signal peptide encompassing an amino acid sequence having methionine at position −26 through alanine at position −1, the CTLA4 portion encompassing an amino acid sequence having methionine at position +1 through aspartic acid at position +124, a junction amino acid residue glutamine at position +125, and the immunoglobulin portion encompassing an amino acid sequence having glutamic acid at position +126 through lysine at position +357.

The soluble CTLA4 mutant molecules of the invention can be obtained by molecular or chemical synthesis methods. The molecular methods may include the following steps: introducing a suitable host cell with a nucleic acid molecule that expresses and encodes the soluble CTLA4 mutant molecule; culturing the host cell so introduced under conditions that permit the host cell to express the mutant molecules; and isolating the expressed mutant molecules. The signal peptide portion of the mutant molecule permits the protein molecules to be expressed on the cell surface and to be secreted by the host cell. The translated mutant molecules can undergo post-translational modification, involving cleavage of the signal peptide to produce a mature protein having the CTLA4 and the immunoglobulin portions. The cleavage may occur after the alanine at position −1, resulting in a mature mutant molecule having methionine at position +1 as the first amino acid (FIG. 7 or 8). Alternatively, the cleavage may occur after the methionine at position −2, resulting in a mature mutant molecule having alanine at position −1 as the first amino acid.

A preferred embodiment is a soluble CTLA4 mutant molecule having the extracellular domain of human CTLA4 linked to all or a portion of a human immunoglobulin molecule (e.g., hinge, CH2 and CH3). This preferred molecule includes the CTLA4 portion of the soluble molecule encompassing an amino acid sequence having methionine at position +1 through aspartic acid at position +124, a junction amino acid residue glutamine at position +125, and the immunoglobulin portion encompassing glutamic acid at position +126 through lysine at position +357. The portion having the extracellular domain of CTLA4 is mutated so that alanine at position +29 is substituted with tyrosine and leucine at position +104 is substituted with glutamic acid. The immunoglobulin portion of the mutant molecule can be mutated, so that the cysteines at positions +130, +136, and +139 are substituted with serine, and the proline at position +148 is substituted with serine. This mutant molecule is designated herein as L104EA29YIg (FIG. 7).

Another embodiment of L104EA29YIg is a mutant molecule having an amino acid sequence having alanine at position −1 through aspartic acid at position +124, a junction amino acid residue glutamine at position +125, and the immunoglobulin portion encompassing glutamic acid at position +126 (e.g., +126 through lysine at position +357). The portion having the extracellular domain of CTLA4 is mutated so that alanine at position +29 is replaced with tyrosine; and leucine at position +104 is replaced with glutamic acid. The immunoglobulin portion of the mutant molecule is mutated so that the cysteines at positions +130, +136, and +139 are replaced with serine, and the proline at position +148 is replaced with serine. This mutant molecule is designated herein as L104EA29YIg (FIG. 7). After the signal sequence has been cleaved, L104EA29YIg can either begin with a methionine at position +1, or begin with alanine at position −1.

Another mutant molecule of the invention is a soluble CTLA4 mutant molecule having the extracellular domain of human CTLA4 linked to the human immunoglobulin molecule (e.g., hinge, CH2 and CH3). This molecule includes the portion of the amino acid sequence encoding CTLA4 starting with methionine at position +1 through aspartic acid at position +124, a junction amino acid residue glutamine at position +125, and the immunoglobulin portion encompassing an amino acid sequence having glutamic acid at position +126 through lysine at position +357. The portion having the extracellular domain of CTLA4 is mutated so that leucine at position +104 is substituted with glutamic acid. The hinge portion of the mutant molecule is mutated so that the cysteines at positions +130, +136, and +139 are substituted with serine, and the proline at position +148 is substituted with serine. This mutant molecule is designated herein as L104EIg (FIG. 8).

Alternatively, an embodiment of L104EIg is a soluble CTLA4 mutant molecule having an extracellular domain of human CTLA4 linked to a human immunoglobulin molecule (e.g., hinge, CH2 and CH3). This preferred molecule includes the CTLA4 portion encompassing an amino acid sequence beginning with alanine at position −1 through aspartic acid at position +124, a junction amino acid residue glutamine at position +125, and the immunoglobulin portion encompassing glutamic acid at position +126 through lysine at position +357. The portion having the extracellular domain of CTLA4 is mutated so that leucine at position +104 is substituted with glutamic acid. The hinge portion of the mutant molecule is mutated so that the cysteines at positions +130, +136, and +139 are substituted with serine, and the proline at position +148 is substituted with serine. This mutant molecule is designated herein as L104EIg (FIG. 8).

Further, the invention provides a soluble CTLA4 mutant molecule having: (a) a first amino acid sequence of a membrane glycoprotein, e.g., CD28, CD86, CD80, CD40, and gp39, which blocks T cell proliferation, fused to a second amino acid sequence; (b) the second amino acid sequence being a fragment of the extracellular domain of mutant CTLA4 which blocks T cell proliferation, such as, for example an amino acid molecule comprising methionine at position +1 through aspartic acid at position +124 (FIG. 7 or 8); and (c) a third amino acid sequence which acts as an identification tag or enhances solubility of the molecule. For example, the third amino acid sequence can consist essentially of amino acid residues of the hinge, CH2 and CH3 regions of a non-immunogenic immunoglobulin molecule.

Examples of suitable immunoglobulin molecules include, but are not limited to, human or monkey immunoglobulin, e.g., C(gamma)1. Other isotypes are also possible.

The invention further provides nucleic acid molecules comprising nucleotide sequences encoding the amino acid sequences corresponding to the soluble CTLA4 mutant molecules of the invention. In one embodiment, the nucleic acid molecule is a DNA (e.g., cDNA) or a hybrid thereof. Alternatively, the nucleic acid molecules are RNA or a hybrids thereof.

Additionally, the invention provides a vector, which comprises the nucleotide sequences of the invention. A host vector system is also provided. The host vector system comprises the vector of the invention in a suitable host cell. Examples of suitable host cells include, but are not limited to, prokaryotic and eukaryotic cells.

The invention includes pharmaceutical compositions for use in the treatment of immune system diseases comprising pharmaceutically effective amounts of soluble CTLA4 mutant molecules. In certain embodiments, the immune system diseases are mediated by CD28- and/or CTLA4-positive cell interactions with CD80 and/or CD86 positive cells. The soluble CTLA4 mutant molecules are preferably CTLA4 molecules having one or more mutations in the extracellular domain of CTLA4. The pharmaceutical composition can include soluble CTLA4 mutant protein molecules and/or nucleic acid molecules, and/or vectors encoding the molecules. In preferred embodiments, the soluble CTLA4 mutant molecules have the amino acid sequence of the extracellular domain of CTLA4 as shown in either FIG. 7 or 8 (L104EA29Y or L104E, respectively). Even more preferably, the soluble CTLA4 mutant molecule is L104EA29YIg as disclosed herein. The compositions may additionally include other therapeutic agents, including, but not limited to, drug toxins, enzymes, antibodies, or conjugates.

The pharmaceutical compositions also preferably include suitable carriers and adjuvants which include any material which when combined with the molecule of the invention (e.g., a soluble CTLA4 mutant molecule, such as, L104EA29Y or L104E) retains the molecule's activity and is non-reactive with the subject's immune system. Examples of suitable carriers and adjuvants include, but are not limited to, human serum albumin; ion exchangers; alumina; lecithin; buffer substances, such as phosphates; glycine; sorbic acid; potassium sorbate; and salts or electrolytes, such as protamine sulfate. Other examples include any of the standard pharmaceutical carriers such as a phosphate buffered saline solution; water, emulsions, such as oil/water emulsion; and various types of wetting agents. Other carriers may also include sterile solutions; tablets, including coated tablets and capsules. Typically such carriers contain excipients such as starch, milk, sugar, certain types of clay, gelatin, stearic acid or salts thereof, magnesium or calcium stearate, talc, vegetable fats or oils, gums, glycols, or other known excipients. Such carriers may also include flavor and color additives or other ingredients. Compositions comprising such carriers are formulated by well known conventional methods. Such compositions may also be formulated within various lipid compositions, such as, for example, liposomes as well as in various polymeric compositions, such as polymer microspheres.

The pharmaceutical compositions of the invention can be administered using conventional modes of administration including, but not limited to, intravenous (i.v.) administration, intraperitoneal (i.p.) administration, intramuscular (i.m.) administration, subcutaneous administration, oral administration, administration as a suppository, or as a topical contact, or the implantation of a slow-release device such as a miniosmotic pump, to the subject.

The pharmaceutical compositions of the invention may be in a variety of dosage forms, which include, but are not limited to, liquid solutions or suspensions, tablets, pills, powders, suppositories, polymeric microcapsules or microvesicles, liposomes, and injectable or infusible solutions. The preferred form depends upon the mode of administration and the therapeutic application.

The most effective mode of administration and dosage regimen for the compositions of this invention depends upon the severity and course of the disease, the patient's health and response to treatment and the judgment of the treating physician. Accordingly, the dosages of the compositions should be titrated to the individual patient.

The soluble CTLA4 mutant molecules may be administered to a subject in an amount and for a time (e.g. length of time and/or multiple times) sufficient to block endogenous B7 (e.g., CD80 and/or CD86) molecules from binding their respective ligands, in the subject. Blockage of endogenous B7/ligand binding thereby inhibits interactions between B7-positive cells (e.g., CD80- and/or CD86-positive cells) with CD28- and/or CTLA4-positive cells. Dosage of a therapeutic agent is dependant upon many factors including, but not limited to, the type of tissue affected, the type of autoimmune disease being treated, the severity of the disease, a subject's health, and a subject's response to the treatment with the agents. Accordingly, dosages of the agents can vary depending on the subject and the mode of administration. The soluble CTLA4 mutant molecules may be administered in an amount between 0.1 to 20.0 mg/kg weight of the patient/day, preferably between 0.5 to 10.0 mg/kg/day. Administration of the pharmaceutical compositions of the invention can be performed over various times. In one embodiment, the pharmaceutical composition of the invention can be administered for one or more hours. In addition, the administration can be repeated depending on the severity of the disease as well as other factors as understood in the art.

The invention further provides methods for producing a protein comprising growing the host vector system of the invention so as to produce the protein in the host and recovering the protein so produced.

Additionally, the invention provides methods for regulating functional CTLA4- and CD28-positive T cell interactions with CD80- and/or CD86-positive cells. The methods comprise contacting the CD80- and/or CD86-positive cells with a soluble CTLA4 mutant molecule of the invention so as to form mutant CTLA4/CD80 and/or mutant CTLA4/CD86 complexes, the complexes interfering with reaction of endogenous CTLA4 antigen with CD80 and/or CD86, and/or the complexes interfering with reaction of endogenous CD28 antigen with CD80 and/or CD86. In one embodiment of the invention, the soluble CTLA4 mutant molecule is a fusion protein that contains at least a portion of the extracellular domain of mutant CTLA4. In another embodiment, the soluble CTLA4 mutant molecule comprises: a first amino acid sequence including the extracellular domain of CTLA4 from the amino acid sequence having methionine at position +1 to aspartic acid at position +124, including at least one mutation; and a second amino acid sequence including the hinge, CH2, and CH3 regions of the human immunoglobulin gamma 1 molecule (FIG. 7 or 8).

In accordance with the practice of the invention, the CD80- or CD86-positive cells are contacted with fragments or derivatives of the soluble CTLA4 mutant molecules of the invention. Alternatively, the soluble CTLA4 mutant molecule is a CD28Ig/CTLA4Ig fusion protein having a first amino acid sequence corresponding to a portion of the extracellular domain of CD28 receptor fused to a second amino acid sequence corresponding to a portion of the extracellular domain of CTLA4 mutant receptor and a third amino acid sequence corresponding to the hinge, CH2 and CH3 regions of human immunoglobulin C-gamma-1.

The soluble CTLA4 mutant molecules are expected to exhibit inhibitory properties in vivo. Under conditions where T cell/APC cell interactions, for example T cell/B cell interactions, are occurring as a result of contact between T cells and APC cells, binding of introduced CTLA4 mutant molecules to react to CD80- and/or CD86-positive cells, for example B cells, may interfere, i.e., inhibit, the T cell/APC cell interactions resulting in regulation of immune responses.

The invention provides methods for downregulating immune responses. Down regulation of an immune response by soluble CTLA4 mutant molecules may be by way of inhibiting or blocking an immune response already in progress or may involve preventing the induction of an immune response. The soluble CTLA4 molecules of the invention may inhibit the functions of activated T cells, such as T lymphocyte proliferation and cytokine secretion, by suppressing T cell responses or by inducing specific tolerance in T cells, or both.

The present invention further provides methods for treating immune system diseases and tolerance induction In particular embodiments, the immune system diseases are mediated by CD28- and/or CTLA4-positive cell interactions with CD80/CD86-positive cells. In a further embodiment, T cell interactions are inhibited. Immune system diseases include, but are not limited to, autoimmune diseases, immunoproliferative diseases, and graft-related disorders. These methods comprise administering to a subject the soluble CTLA4 mutant molecules of the invention to regulate T cell interactions with the CD80- and/or CD86-positive cells. Alternatively, a CTLA4 mutant hybrid having a membrane glycoprotein joined to a CTLA4 mutant molecule can be administered. Examples of graft-related diseases include graft versus host disease (GVHD) (e.g., such as may result from bone marrow transplantation, or in the induction of tolerance), immune disorders associated with graft transplantation rejection, chronic rejection, and tissue or cell allo- or xenografts, including solid organs, skin, islets, muscles, hepatocytes, neurons. Examples of immunoproliferative diseases include, but are not limited to, psoriasis; T cell lymphoma; T cell acute lymphoblastic leukemia; testicular angiocentric T cell lymphoma; benign lymphocytic angiitis; and autoimmune diseases such as lupus (e.g., lupus erythematosus, lupus nephritis), Hashimoto's thyroiditis, primary myxedema, Graves' disease, pernicious anemia, autoimmune atrophic gastritis, Addison's disease, diabetes (e.g. insulin dependent diabetes mellitis, type I diabetes mellitis), good pasture's syndrome, myasthenia gravis, pemphigus, Crohn's disease, sympathetic ophthalmia, autoimmune uveitis, multiple sclerosis, autoimmune hemolytic anemia, idiopathic thrombocytopenia, primary biliary cirrhosis, chronic action hepatitis, ulceratis colitis, Sjogren's syndrome, rheumatic diseases (e.g., rheumatoid arthritis), polymyositis, scleroderma, and mixed connective tissue disease.

The present invention further provides a method for inhibiting solid organ and/or tissue transplant rejections by a subject, the subject being a recipient of transplant tissue. Typically, in tissue transplants, rejection of the graft is initiated through its recognition as foreign by T cells, followed by an immune response that destroys the graft. The soluble CTLA4 mutant molecules of this invention, by inhibiting T lymphocyte proliferation and/or cytokine secretion, may result in reduced tissue destruction and induction of antigen-specific T cell unresponsiveness may result in long-term graft acceptance without the need for generalized immunosuppression. Furthermore, the soluble CTLA4 mutant molecules of the invention can be administered with other pharmaceuticals including, but not limited to, corticosteroids, cyclosporine, rapamycin, mycophenolate mofetil, azathioprine, tacrolismus, basiliximab, and/or other biologics.

The present invention also provides methods for inhibiting graft versus host disease in a subject. This method comprises administering to the subject a soluble CTLA4 mutant molecule of the invention, alone or together, with further additional ligands, reactive with IL-2, IL-4, or 7-interferon. For example, a soluble CTLA mutant molecule of this invention may be administered to a bone marrow transplant recipient to inhibit the alloreactivity of donor T cells. Alternatively, donor T cells within a bone marrow graft may be tolerized to a recipient's alloantigens ex vivo prior to transplantation.

Inhibition of T cell responses by soluble CTLA4 mutant molecules may also be useful for treating autoimmune disorders. Many autoimmune disorders result from inappropriate activation of T cells that are reactive against autoantigens, and which promote the production of cytokines and autoantibodies that are involved in the pathology of the disease. Administration of a soluble CTLA4 mutant molecule in a subject suffering from or susceptible to an autoimmune disorder may prevent the activation of autoreactive T cells and may reduce or eliminate disease symptoms. This method may also comprise administering to the subject a soluble CTLA4 mutant molecule of the invention, alone or together, with further additional ligands, reactive with IL-2, IL-4, or γ-interferon.

The invention further encompasses the use of the soluble CTLA4 mutant molecules together with other immunosuppressants, e.g., cyclosporin (see Mathiesen, in: "Prolonged Survival and Vascularization of Xenografted Human Glioblastoma Cells in the Central Nervous System of Cyclosporin A-Treated Rats" (1989) *Cancer Lett.,* 44:151-156), prednisone, azathioprine, and methotrexate (R. Handschumacher "Chapter 53: *Drugs Used for Immunosuppression*" pages 1264-1276). Other immunosuppressants are possible. For example, for the treatment of rheumatoid arthritis, soluble CTLA4 mutant molecules can be administered with pharmaceuticals including, but not limited to, corticosteroids, nonsteroidal antiinflammatory drugs/Cox-2 inhibitors, methotrexate, hydroxychloroquine, sulphasalazopryine, gold salts, etanercept, infliximab, anakinra, azathioprine, and/or other biologics like anti-TNF. For the treatment of systemic lupus eryhtematohosus, soluble CTLA4 mutant molecules can be administered with pharmaceuticals including, but not limited to, corticosteroids, cytoxan, azathioprine, hydroxychloroquine, mycophenolate mofetil, and/or other biologics. Further, for the treatment of multiple sclerosis, soluble CTLA4 mutant molecules can be administered with pharmaceuticals including, but not limited to, corticosteroids, interferon beta-1a, interferon beta-1b, glatiramer acetate, mitoxantrone hydrochloride, and/or other biologics.

The soluble CTLA4 mutant molecules (preferably, L104EA29YIg) can also be used in combination with one or more of the following agents to regulate an immune response: soluble gp39 (also known as CD40 ligand (CD40L), CD154, T-BAM, TRAP), soluble CD29, soluble CD40, soluble CD80, soluble CD86, soluble CD28, soluble CD56, soluble Thy-1, soluble CD3, soluble TCR, soluble VLA-4, soluble VCAM-1, soluble LECAM-1, soluble ELAM-1, soluble CD44, antibodies reactive with gp39, antibodies reactive with CD40, antibodies reactive with B7, antibodies reactive with CD28, antibodies reactive with LFA-1, antibodies reactive with LFA-2, antibodies reactive with IL-2, antibodies reactive with IL-12, antibodies reactive with IFN-gamma, antibodies reactive with CD2, antibodies reactive with CD48, antibodies reactive with any ICAM (e.g., ICAM-2), antibodies reactive with CTLA4, antibodies reactive with Thy-1, antibodies reactive with CD56, antibodies reactive with CD3, antibodies reactive with CD29, antibodies reactive with TCR, antibodies reactive with VLA-4, antibodies reactive with VCAM-1, antibodies reactive with LECAM-1, antibodies reactive with ELAM-1, antibodies reactive with CD44. In certain embodiments, monoclonal antibodies are preferred. In other embodiments, antibody fragments are preferred. As persons skilled in the art will readily understand, the combination can include the soluble CTLA4 mutant molecules of the invention and one other immunosuppressive agent, the soluble CTLA4 mutant molecules with two other immunosuppressive agents, the soluble CTLA4 mutant molecules with three other immunosuppressive agents, etc. The determination of the optimal combination and dosages can be determined and optimized using methods well known in the art.

Some specific combinations include the following: L104EA29YIg and CD80 mAbs; L104EA29YIg and CD86 mAbs; L104EA29YIg, CD80 mAbs, and CD86 mAbs; L104EA29YIg and gp39 mAbs; L104EA29YIg and CD40 mAbs; L104EA29YIg and CD28 mAbs; L104EA29YIg, CD80 and CD86 mAbs, and gp39 mAbs; L104EA29YIg, CD80 and CD86 mAbs and CD40 mAbs; and L104EA29YIg, anti-LFA1 mAb, and anti-gp39 mAb. A specific example of a gp39 mAb is MR1. Other combinations will be readily appreciated and understood by persons skilled in the art.

The soluble CTLA4 mutant molecules of the invention, for example L104EA29Y, may be administered as the sole active ingredient or together with other drugs in immunomodulating regimens or other anti-inflammatory agents e.g. for the treatment or prevention of allo- or xenograft acute or chronic rejection or inflammatory or autoimmune disorders, or to induce tolerance. For example, it may be used in combination with a calcineurin inhibitor, e.g. cyclosporin A or FK506; an immunosuppressive macrolide, e.g. rapamycine or a derivative thereof; e.g. 40-O-(2-hydroxyl)ethyl-rapamycin, a lymphocyte homing agent, e.g. FTY720 or an analog thereof; corticosteroids; cyclophosphamide; azathioprene; methotrexate; leflunomide or an analog thereof; mizoribine; mycophenolic acid; mycophenolate mofetil; 15-deoxyspergualine or an analog thereof; immunosuppressive monoclonal antibodies, e.g., monoclonal antibodies to leukocyte receptors, e.g., MHC, CD2, CD3, CD4, CD 11a/CD18, CD7, CD25, CD 27, B7, CD40, CD45, CD58, CD 137, ICOS, CD 150 (SLAM), OX40, 4-1BB or their ligands; or other immunomodulatory compounds, e.g. CTLA4/CD28-Ig, or other adhesion molecule inhibitors, e.g. mAbs or low molecular weight inhibitors including LFA-1 antagonists, Selectin antagonists and VLA-4 antagonists. The compound is particularly useful in combination with a compound which interferes with CD40 and its ligand, e.g. antibodies to CD40 and antibodies to CD40-L, e.g. in the above described indications, e.g the induction of tolerance.

Where the soluble CTLA4 mutant molecules of the invention are administered in conjunction with other immunosuppressive/immunomodulatory or anti-inflammatory therapy, e.g as hereinabove specified, dosages of the co-administered immunosuppressant, immunomodulatory or anti-inflammatory compound will of course vary depending on the type of co-drug employed, e.g. whether it is a steroid or a cyclosporine, on the specific drug employed, on the condition being treated and so forth.

In accordance with the foregoing the present invention provides in a yet further aspect methods as defined above comprising co-administration, e.g. concomitantly or in sequence, of a therapeutically effective amount of soluble CTLA4 mutant molecules of the invention, L104EA29YIg, in free form or in pharmaceutically acceptable salt form, and a second drug substance, said second drug substance being an immunosuppressant, immunomodulatory or anti-inflammatory drug, e.g. as indicated above. Further provided are therapeutic combinations, e.g. a kit, e.g. for use in any method as defined above, comprising a L104EA29YIg, in free form or in pharmaceutically acceptable salt form, to be used concomitantly or in sequence with at least one pharmaceutical composition comprising an immunosuppressant, immunomodulatory or anti-inflammatory drug. The kit may comprise instructions for its administration.

Methods for Producing the Molecules of the Invention

Expression of CTLA4 mutant molecules can be in prokaryotic cells. Prokaryotes most frequently are represented by various strains of bacteria. The bacteria may be a gram positive or a gram negative. Typically, gram-negative bacteria such as *E. coli* are preferred. Other microbial strains may also be used.

Sequences encoding CTLA4 mutant molecules can be inserted into a vector designed for expressing foreign sequences in prokaryotic cells such as *E. coli*. These vectors can include commonly used prokaryotic control sequences which are defined herein to include promoters for transcription initiation, optionally with an operator, along with ribosome binding site sequences, include such commonly used promoters as the beta-lactamase (penicillinase) and lactose (lac) promoter systems (Chang, et al., (1977) *Nature* 198: 1056), the tryptophan (trp) promoter system (Goeddel, et al., (1980) *Nucleic Acids Res.* 8:4057) and the lambda derived PL promoter and N-gene ribosome binding site (Shimatake, et al., (1981) *Nature* 292:128).

Such expression vectors will also include origins of replication and selectable markers, such as a beta-lactamas or neomycin phosphotransferase gene conferring resistance to antibiotics, so that the vectors can replicate in bacteria and cells carrying the plasmids can be selected for when grown in the presence of antibiotics, such as ampicillin or kanamycin.

The expression plasmid can be introduced into prokaryotic cells via a variety of standard methods, including but not limited to CaCl$_2$-shock (Cohen, (1972) *Proc. Natl. Acad. Sci. USA* 69:2110, and Sambrook et al. (eds.), *"Molecular Cloning: A Laboratory Manual"*, 2nd Edition, Cold Spring Harbor Press, (1989)) and electroporation.

In accordance with the practice of the invention, eukaryotic cells are also suitable host cells. Examples of eukaryotic cells include any animal cell, whether primary or immortalized, yeast (e.g., *Saccharomyces cerevisiae*, Schizosaccharomyces pombe, and *Pichia pastoris*), and plant cells. Myeloma, COS and CHO cells are examples of animal cells that may be used as hosts. Particular CHO cells include, but are not limited to, DG44 (Chasin, et al., 1986 *Som. Cell. Molec. Genet.* 12:555-556; Kolkekar 1997 *Biochemistry* 36:10901-10909), CHO-k1 (ATCC No. CCL-61), CHO-KI Tet-On cell line (Clontech), CHO designated ECACC 85050302 (CAMR, Salisbury, Wiltshire, UK), CHO clone 13 (GEIMG, Genova, IT), CHO clone B (GEIMG, Genova, IT), CHO-KI/SF designated ECACC 93061607 (CAMR, Salisbury, Wiltshire, UK), and RR-CHOK1 designated ECACC 92052129 (CAMR, Salisbury, Wiltshire, UK). Exemplary plant cells include tobacco (whole plants, cell culture, or callus), corn, soybean, and rice cells. Corn, soybean, and rice seeds are also acceptable.

Nucleic acid sequences encoding the CTLA4 mutant molecules can also be inserted into a vector designed for expressing foreign sequences in a eukaryotic host. The regulatory elements of the vector can vary according to the particular eukaryotic host.

Commonly used eukaryotic control sequences for use in expression vectors include promoters and control sequences compatible with mammalian cells such as, for example, CMV promoter (CDM8 vector) and avian sarcoma virus (ASV) (LN vector). Other commonly used promoters include the early and late promoters from Simian Virus 40 (SV40) (Fiers, et al., (1973) *Nature* 273:113), or other viral promoters such as those derived from polyoma, Adenovirus 2, and bovine papilloma virus. An inducible promoter, such as hMTII (Karin, et al., (1982) *Nature* 299:797-802) may also be used.

Vectors for expressing CTLA4 mutant molecules in eukaryotes may also carry sequences called enhancer regions. These are important in optimizing gene expression and are found either upstream or downstream of the promoter region.

Examples of expression vectors for eukaryotic host cells include, but are not limited to, vectors for mammalian host cells (e.g., BPV-1, pHyg, pRSV, pSV2, pTK2 (Maniatis); pIRES (Clontech); pRc/CMV2, pRc/RSV, pSFV1 (Life Technologies); pVPakc Vectors, pCMV vectors, pSG5 vectors (Stratagene)), retroviral vectors (e.g., pFB vectors (Stratagene)), pCDNA-3 (Invitrogen) or modified forms thereof, adenoviral vectors; Adeno-associated virus vectors, baculovirus vectors, yeast vectors (e.g., pESC vectors (Stratagene)).

Nucleic acid sequences encoding CTLA4 mutant molecules can integrate into the genome of the eukaryotic host cell and replicate as the host genome replicates. Alternatively, the vector carrying CTLA4 mutant molecules can contain origins of replication allowing for extrachromosomal replication.

For expressing the nucleic acid sequences in *Saccharomyces cerevisiae*, the origin of replication from the endogenous yeast plasmid, the 2μ circle can be used. (Broach, (1983) *Meth. Enz.* 101:307). Alternatively, sequences from the yeast genome capable of promoting autonomous replication can be used (see, for example, Stinchcomb et al., (1979) *Nature* 282:39); Tschemper et al., (1980) *Gene* 10:157; and Clarke et al., (1983) *Meth. Enz.* 101:300).

Transcriptional control sequences for yeast vectors include promoters for the synthesis of glycolytic enzymes (Hess et al., (1%968)*J. Adv. Enzyme Reg.* 7:149; Holland et al., (1978) *Biochemistry* 17:4900). Additional promoters known in the art include the CMV promoter provided in the CDM8 vector (Toyama and Okayama, (1990) *FEBS* 268: 217-221); the promoter for 3-phosphoglycerate kinase (Hitzeman et al., (1980) *J. Biol. Chem.* 255:2073), and those for other glycolytic enzymes.

Other promoters are inducible because they can be regulated by environmental stimuli or the growth medium of the cells. These inducible promoters include those from the genes for heat shock proteins, alcohol dehydrogenase 2, isocytochrome C, acid phosphatase, enzymes associated with nitrogen catabolism, and enzymes responsible for maltose and galactose utilization.

Regulatory sequences may also be placed at the 3' end of the coding sequences. These sequences may act to stabilize messenger RNA. Such terminators are found in the 3' untranslated region following the coding sequences in several yeast-derived and mammalian genes.

Exemplary vectors for plants and plant cells include, but are not limited to, *Agrobacterium* T$_i$ plasmids, cauliflower mosaic virus (CaMV), and tomato golden mosaic virus (TGMV).

General aspects of mammalian cell host system transformations have been described by Axel (U.S. Pat. No. 4,399, 216 issued Aug. 16, 1983). Mammalian cells can be transformed by methods including but not limited to, transfection in the presence of calcium phosphate, microinjection, electroporation, or via transduction with viral vectors.

Methods for introducing foreign DNA sequences into plant and yeast genomes include (1) mechanical methods, such as microinjection of DNA into single cells or protoplasts, vortexing cells with glass beads in the presence of DNA, or shooting DNA-coated tungsten or gold spheres into cells or protoplasts; (2) introducing DNA by making cell membranes permeable to macromolecules through polyethylene glycol treatment or subjection to high voltage electrical pulses (electroporation); or (3) the use of liposomes (containing cDNA) which fuse to cell membranes.

Expression of CTLA4 mutant molecules can be detected by methods known in the art. For example, the mutant molecules can be detected by Coomassie staining SDS-PAGE gels and immunoblotting using antibodies that bind CTLA4. Protein recovery can be performed using standard protein purification means, e.g., affinity chromatography or ion-exchange chromatography, to yield substantially pure product (R. Scopes in: "*Protein Purification, Principles and Practice*", Third Edition, Springer-Verlag (1994)).

The invention further provides soluble CTLA4 mutant molecules produced above herein.

CTLA4Ig Codon-Based Mutagenesis

In one embodiment, site-directed mutagenesis and a novel screening procedure were used to identify several mutations in the extracellular domain of CTLA4 that improve binding avidity for CD86. In this embodiment, mutations were carried out in residues in the regions of the extracellular domain of CTLA4 from serine 25 to arginine 33, the C' strand (alanine 49 and threonine 51), the F strand (lysine 93, glutamic acid 95 and leucine 96), and in the region from methionine 97 through tyrosine 102, tyrosine 103 through glycine 107 and in the G strand at positions glutamine 111, tyrosine 113 and isoleucine 115. These sites were chosen based on studies of chimeric CD28/CTLA4 fusion proteins (Peach et al., *J. Exp. Med.*, 1994, 180:2049-2058), and on a model predicting which amino acid residue side chains would be solvent exposed, and a lack of amino acid residue identity or homology at certain positions between CD28 and CTLA4. Also, any residue which is spatially in close proximity (5 to 20 Angstrom Units) to the identified residues is considered part of the present invention.

To synthesize and screen soluble CTLA4 mutant molecules with altered affinities for CD80 and/or CD86, a two-step strategy was adopted. The experiments entailed first generating a library of mutations at a specific codon of an extracellular portion of CTLA4 and then screening these by BIAcore analysis to identify mutants with altered reactivity to CD80 or CD86. The Biacore assay system (Pharmacia, Piscataway, N.J.) uses a surface plasmon resonance detector system that essentially involves covalent binding of either CD80Ig or CD86Ig to a dextran-coated sensor chip which is located in a detector. The test molecule can then be injected into the chamber containing the sensor chip and the amount of complementary protein that binds can be assessed based on the change in molecular mass which is physically associated with the dextran-coated side of the sensor chip; the change in molecular mass can be measured by the detector system.

Advantages Of The Invention

Because CTLA4 binding to CD80 and CD86 is characterized by rapid "on" rates and rapid dissociation ("off") rates, and because CTLA4Ig-CD86 complexes dissociate approximately 5- to 8-fold more rapidly than CTLA4Ig-CD80 complexes, it was reasoned that slowing the rate of dissociation of CTLA4Ig from CD80 and/or CD86 would result in molecules with more potent immunosuppressive properties. Thus, soluble CTLA4 mutant molecules having a higher avidity for CD80- or CD86-positive cells compared to wild type CTLA4, or non-mutated forms of CTLA4Ig, are expected to block the priming of antigen specific activated cells with higher efficiency than wild type CTLA4 or non-mutated forms of CTLA4Ig.

Further, production costs for CTLA4Ig are very high. The high avidity mutant CTLA4Ig molecules having higher potent immunosuppressive properties can be used in the clinic, at considerably lower doses than non-mutated CTLA4Ig, to achieve similar levels of immunosuppression. Thus, soluble CTLA4 mutant molecules, e.g., L104EA29YIg, may be very cost effective.

The following examples are presented to illustrate the present invention and to assist one of ordinary skill in making and using the same. The examples are not intended in any way to otherwise limit the scope of the invention.

EXAMPLES

Example 1

This example provides a description of the methods used to generate the nucleotide sequences encoding the soluble CTLA4 mutant molecules of the invention. A single-site mutant L104EIg was generated and tested for binding kinetics for CD80 and/or CD86. The L104EIg nucleotide sequence was used as a template to generate the double-site mutant CTLA4 sequence, L104EA29YIg, which was tested for binding kinetics for CD80 and/or CD86.

CTLA4Ig Codon Based Mutagenesis

A mutagenesis and screening strategy was developed to identify mutant CTLA4Ig molecules that had slower rates of dissociation ("off" rates) from CD80 and/or CD86 molecules. Single-site mutant nucleotide sequences were generated using CTLA4Ig (U.S. Pat. Nos. 5,844,095; 5,851,795; and 5,885,796; ATCC Accession No. 68629) as a template. Mutagenic oligonucleotide PCR primers were designed for random mutagenesis of a specific cDNA codon by allowing any base at positions 1 and 2 of the codon, but only guanine or thymine at position 3 (XXG/T; also known as NNG/T). In this manner, a specific codon encoding an amino acid could be randomly mutated to code for each of the 20 amino acids. In that regard, XXG/T mutagenesis yields 32 potential codons encoding each of the 20 amino acids. PCR products encoding mutations in close proximity to -M97-G107 of CTLA4Ig (see FIG. 7 or 8), were digested with SacI/XbaI and subcloned into similarly cut CTLA4Ig πLN (also known as piLN) expression vector. This method was used to generate the single-site CTLA4 mutant molecule L104EIg (FIG. 8).

For mutagenesis in proximity to S25-R33 of CTLA4Ig, a silent NheI restriction site was first introduced 5' to this loop, by PCR primer-directed mutagenesis. PCR products were digested with NheI/XbaI and subcloned into similarly cut CTLA4Ig or L104EIg expression vectors. This method was used to generate the double-site CTLA4 mutant molecule L104EA29YIg (FIG. 7). In particular, the nucleic acid molecule encoding the single-site CTLA4 mutant molecule, L104EIg, was used as a template to generate the double-site CTLA4 mutant molecule, L104EA29YIg. The piLN vector having the L104EA29YIg is shown in FIG. 12.

Example 2

The following provides a description of the screening methods used to identify the single- and double-site mutant CTLA4 polypeptides, expressed from the constructs described in Example 1, that exhibited a higher binding avidity for CD80 and CD86 antigens, compared to non-mutated CTLA4Ig molecules.

Current in vitro and in vivo studies indicate that CTLA4Ig by itself is unable to completely block the priming of antigen specific activated T cells. In vitro studies with CTLA4Ig and either monoclonal antibody specific for CD80 or CD86 measuring inhibition of T cell proliferation indicate that anti-CD80 monoclonal antibody did not augment CTLA4Ig inhibition. However, anti-CD86 monoclonal antibody did augment the inhibition, indicating that CTLA4Ig was not as effective at blocking CD86 interactions. These data support earlier findings by Linsley et al. (*Immunity*, (1994), 1:793-801) showing inhibition of CD80-mediated cellular responses required approximately 100 fold lower CTLA4Ig concentrations than for CD86-mediated responses. Based on these findings, it was surmised that soluble CTLA4 mutant molecules having a higher avidity for CD86 than wild type CTLA4 should be better able to block the priming of antigen specific activated cells than CTLA4Ig.

To this end, the soluble CTLA4 mutant molecules described in Example 1 above were screened using a novel screening procedure to identify several mutations in the extracellular domain of CTLA4 that improve binding avidity for CD80 and CD86. This screening strategy provided an effective method to directly identify mutants with apparently slower "off" rates without the need for protein purification or quantitation since "off" rate determination is concentration independent (O'Shannessy et al., (1993) *Anal. Biochem.*, 212:457-468).

COS cells were transfected with individual miniprep purified plasmid DNA and propagated for several days. Three day conditioned culture media was applied to BIAcore biosensor chips (Pharmacia Biotech AB, Uppsala, Sweden) coated with soluble CD80Ig or CD86Ig. The specific binding and dissociation of mutant proteins was measured by surface plasmon resonance (O'Shannessy, D. J., et al., (1993)*Anal. Biochem.* 212:457-468). All experiments were run on BIAcore™ or BIAcore™ 2000 biosensors at 25° C. Ligands were immobilized on research grade NCM5 sensor chips (Pharmacia) using standard N-ethyl-N'-(dimethylaminopropyl) carbodiimidN-hydroxysuccinimide coupling (Johnsson, B., et al. (1991) *Anal. Biochem.* 198: 268-277; Khilko, S. N., et al. (1993) *J. Biol. Chem.* 268: 5425-15434).

Screening Method

COS cells grown in 24 well tissue culture plates were transiently transfected with DNA encoding mutant CTLA4Ig. Culture media containing secreted soluble mutant CTLA4Ig was collected 3 days later.

Conditioned COS cell culture media was allowed to flow over BIAcore biosensor chips derivatized with CD86Ig or CD80Ig (as described in Greene et al., 1996 *J. Biol. Chem.* 271:26762-26771), and mutant molecules were identified with "off" rates slower than that observed for wild type CTLA4Ig. The cDNAs corresponding to selected media samples were sequenced and DNA was prepared to perform larger scale COS cell transient transfection, from which mutant CTLA4Ig protein was prepared following protein A purification of culture media.

BIAcore analysis conditions and equilibrium binding data analysis were performed as described in J. Greene et al. 1996 *J. Biol. Chem.* 271:26762-26771, and as described herein.

BIAcore Data Analysis

Senosorgram baselines were normalized to zero response units (RU) prior to analysis. Samples were run over mock-derivatized flow cells to determine background response unit (RU) values due to bulk refractive index differences between solutions. Equilibrium dissociation constants ($K_d$) were calculated from plots of $R_{eq}$ versus C, where $R_{eq}$ is the steady-state response minus the response on a mock-derivatized chip, and C is the molar concentration of analyte. Binding curves were analyzed using commercial nonlinear curve-fitting software (Prism, GraphPAD Software).

Experimental data were first fit to a model for a single ligand binding to a single receptor (1-site model, i.e., a simple langmuir system, $A+B \leftrightarrows AB$), and equilibrium association constants ($K_d=[A]\cdot[B]\backslash[AB]$) were calculated from the equation $R=R_{max}\cdot C/(K_d+C)$. Subsequently, data were fit to the simplest two-site model of ligand binding (i.e., to a receptor having two non-interacting independent binding sites as described by the equation $R=R_{max1}\cdot C\backslash(K_{d1}+C)+R_{max2}\cdot C\backslash(K_{d2}+C)$).

The goodness-of-fits of these two models were analyzed visually by comparison with experimental data and statistically by an F test of the sums-of-squares. The simpler one-site model was chosen as the best fit, unless the two-site model fit significantly better (p<0.1).

Association and disassociation analyses were performed using BIA evaluation 2.1 Software (Pharmacia). Association rate constants $k_{on}$ were calculated in two ways, assuming both homogenous single-site interactions and parallel two-site interactions. For single-site interactions, $k_{on}$ values were calculated according to the equation $R_t=R_{eq}(1-\exp^{-ks(t-t_0)})$, where $R_t$ is a response at a given time, t; $R_{eq}$ is the steady-state response; to is the time at the start of the injection; and $k_s=dR/dt=k_{on}\cdot Ck_{off}$ and where C is a concentration of analyte, calculated in terms of monomeric binding sites. For two-site interactions $k_{on}$ values were calculated according to the equation $R_t=R_{eq1}(1-\exp^{-ks1(t-t_0)})+R_{eq2}(1-\exp^{ks2(t-t_0)})$. For each model, the values of $k_{on}$ were determined from the calculated slope (to about 70% maximal association) of plots of $k_s$ versus C.

Dissociation data were analyzed according to one site (AB=A+B) or two sites (AiBj=Ai+Bj) models, and rate constants ($k_{off}$) were calculated from best fit curves. The binding site model was used except when the residuals were greater than machine background (2-10 RU, according to machine), in which case the two-binding site model was employed. Half-times of receptor occupancy were calculated using the relationship $t_{1/2}=0.693/k_{off}$.

Flow Cytometry

Murine mAb L307.4 (anti-CD80) was purchased from Becton Dickinson (San Jose, Calif.) and IT2.2 (anti-B7-0 [also known as CD86]), from Pharmingen (San Diego, Calif.). For immunostaining, CD80-positive and/or CD86-positive CHO cells were removed from their culture vessels by incubation in phosphate-buffered saline (PBS) containing 10 mM EDTA. CHO cells ($1-10 \times 10^5$) were first incubated with mAbs or immunoglobulin fusion proteins in DMEM containing 10% fetal bovine serum (FBS), then washed and incubated with fluorescein isothiocyanate-conjugated goat anti-mouse or anti-human immunoglobulin second step reagents (Tago, Burlingame, Calif.). Cells were given a final wash and analyzed on a FACScan (Becton Dickinson).

SDS-PAGE and Size Exclusion Chromatography

SDS-PAGE was performed on Tris/glycine 4-20% acrylamide gels (Novex, San Diego, Calif.). Analytical gels were stained with Coomassie Blue, and images of wet gels were obtained by digital scanning. CTLA4Ig (25 µg) and L104EA29YIg (25 µg) were analyzed by size exclusion chromatography using a TSK-GEL G300 SW$_{XL}$ column (7.8×300 mm, Tosohaas, Montgomeryville, Pa.) equilibrated in phosphate buffered saline containing 0.02% NAN$_3$ at a flow rate of 1.0 ml/min.

CTLA4X$_{C120S}$ and L104EA29YX$_{C120S}$.

Single chain CTLA4X$_{C120S}$ was prepared as previously described (Linsley et al., (1995), *J. Biol. Chem.*, 270:15417-

15424). Briefly, an oncostatin M CTLA4 (OMCTLA4) expression plasmid was used as a template, the forward primer,
GAGGTGATAAAGCTTCACCAATGGTGTACTGCT-CACACAG was chosen to match sequences in the vector, and the reverse primer,
GTGGTGTATrGGTCTAGATCAATCA-GAATCTGGGCACGGTTC corresponded to the last seven amino acids (i.e. amino acids 118-124) in the extracellular domain of CTLA4, and contained a restriction enzyme site, and a stop codon (TGA). The reverse primer specified a C120S (cysteine to serine at position 120) mutation. In particular, the nucleotide sequence GCA (nucleotides 34-36) of the reverse primer shown above is replaced with one of the following nucleotide sequences: AGA, GGA, TGA, CGA, ACT, or GCT. As persons skilled in the art will understand, the nucleotide sequence GCA is a reversed complementary sequence of the codon TGC for cysteine. Similarly, the nucleotide sequences AGA, GGA, TGA, CGA, ACT, or GCT are the reversed complementary sequences of the codons for serine. Polymerase chain reaction products were digested with HindIII/XbaI and directionally subcloned into the expression vector πLN (Bristol-Myers Squibb Company, Princeton, N.J.). L104EA29YX$_{C120S}$ was prepared in an identical manner. Each construct was verified by DNA sequencing.

Identification and Biochemical Characterization of High Avidity Mutants

Twenty four amino acids were chosen for mutagenesis and the resulting ~2300 mutant proteins assayed for CD86Ig binding by surface plasmon resonance (SPR; as described, supra). The predominant effects of mutagenesis at each site are summarized in Table II. Random mutagenesis of some amino acids in the S25-R33 apparently did not alter ligand binding. Mutagenesis of E31 and R33 and residues M97-Y102 apparently resulted in reduced ligand binding. Mutagenesis of residues, S25, A29, and T30, K93, L96, Y103, L104, and G105, resulted in proteins with slow "on" and/or slow "off" rates. These results confirm previous findings that residues in the S25-R33 region, and residues in or near M97-Y102 influence ligand binding (Peach et al., (1994) *J. Exp. Med.,* 180:2049-2058.

Mutagenesis of sites S25, T30, K93, L96, Y103, and G105 resulted in the identification of some mutant proteins that had slower "off" rates from CD86Ig. However, in these instances, the slow "off" rate was compromised by a slow "on" rate which resulted in mutant proteins with an overall avidity for CD86Ig that was apparently similar to that seen with wild type CTLA4Ig. In addition, mutagenesis of K93 resulted in significant aggregation which may have been responsible for the kinetic changes observed.

Random mutagenesis of L104 followed by COS cell transfection and screening by SPR of culture media samples over immobilized CD86Ig yielded six media samples containing mutant proteins with approximately 2-fold slower "off" rates than wild type CTLA4Ig. When the corresponding cDNA of these mutants were sequenced, each was found to encode a leucine to glutamic acid mutation (L104E). Apparently, substitution of leucine 104 to aspartic acid (L104D) did not affect CD86Ig binding.

Mutagenesis was then repeated at each site listed in Table II, this time using L104E as the PCR template instead of wild type CTLA4Ig, as described above. SPR analysis, again using immobilized CD86Ig, identified six culture media samples from mutagenesis of alanine 29 with proteins having approximately 4-fold slower "off" rates than wild type CTLA4Ig. The two slowest were tyrosine substitutions (L104EA29Y), two were leucine (L104EA29L), one was tryptophan (L104EA29W), and one was threonine (L104EA29T). Apparently, no slow "off" rate mutants were identified when alanine 29 was randomly mutated, alone, in wild type CTLA4Ig.

The relative molecular mass and state of aggregation of purified L104E and L104EA29YIg was assessed by SDS-PAGE and size exclusion chromatography. L104EA29YIg (~1 μg; lane 3) and L104EIg (~1 μg; lane 2) apparently had the same electrophoretic mobility as CTLA4Ig (~1 μg; lane 1) under reducing (~50 kDa; +βME; plus 2-mercaptoethanol) and non-reducing (~100 kDa; −βME) conditions (FIG. 10A). Size exclusion chromatography demonstrated that L04EA29YIg (FIG. 10C) apparently had the same mobility as dimeric CTLA4Ig (FIG. 10B). The major peaks represent protein dimer while the faster eluting minor peak in FIG. 10B represents higher molecular weight aggregates. Approximately 5.0% of CTLA4Ig was present as higher molecular weight aggregates but there was no evidence of aggregation of L104EA29YIg or L104EIg. Therefore, the stronger binding to CD86Ig seen with L104EIg and L04EA29YIg could not be attributed to aggregation induced by mutagenesis.

Equilibrium and Kinetic Binding Analysis

Equilibrium and kinetic binding analysis was performed on protein A purified CTLA4Ig, L104EIg, and L104EA29YIg using surface plasmon resonance (SPR). The results are shown in Table L Observed equilibrium dissociation constants ($K_d$; Table I) were calculated from binding curves generated over a range of concentrations (5.0-200 nM). L104EA29YIg binds more strongly to CD86Ig than does L104EIg or CTLA4Ig. The lower $K_d$ of L104EA29YIg (3.21 nM) than L104EIg (6.06 nM) or CTLA4Ig (13.9 nM) indicates higher binding avidity of L104EA29YIg to CD86Ig. The lower $K_d$ of L104EA29YIg (3.66 nM) than L104EIg (4.47 nM) or CTLA4Ig (6.51 nM) indicates higher binding avidity of L104EA29YIg to CD80Ig.

Kinetic binding analysis revealed that the comparative "on" rates for CTLA4Ig, L104EIg, and L104EA29YIg binding to CD80 were similar, as were the "on" rates for CD86Ig (Table I). However, "off" rates for these molecules were not equivalent (Table I). Compared to CTLA4Ig, L104EA29YIg had approximately 2-fold slower "of" rate from CD80Ig, and approximately 4-fold slower "off" rate from CD86Ig. L104E had "off" rates intermediate between L104EA29YIg and CTLA4Ig. Since the introduction of these mutations did not significantly affect "on" rates, the increase in avidity for CD80Ig and CD86Ig observed with L104EA29YIg was likely primarily due to a decrease in "off" rates.

To determine whether the increase in avidity of L104EA29YIg for CD86Ig and CD80Ig was due to the mutations affecting the way each monomer associated as a dimer, or whether there were avidity enhancing structural changes introduced into each monomer, single chain constructs of CTLA4 and L104EA29Y extracellular domains were prepared following mutagenesis of cysteine 120 to serine as described supra, and by Linsley et al., (1995) *J. Biol. Chem.,* 270:15417-15424. The purified proteins CTLA4X$_{C120S}$ and L104EA29YX$_{C120S}$ were shown to be monomeric by gel permeation chromatography (Linsley et al., (1995), supra), before their ligand binding properties were analyzed by SPR Results showed that binding affinity of both monomeric proteins for CD86Ig was approximately 35-80-fold less than that seen for their respective dimers (Table I). This supports previously published data establishing that dimerization of CTLA4 was required for high avidity ligand binding (Greene et al., (1996) *J. Biol. Chem.,* 271:26762-26771).

L104EA29YX$_{C120S}$ bound with approximately 2-fold higher affinity than CTLA4X$_{C120S}$ to both CD80Ig and CD86Ig. The increased affinity was due to approximately 3-fold slower rate of dissociation from both ligands. Therefore, stronger ligand binding by L104EA29Y was most likely due to avidity enhancing structural changes that had been introduced into each monomeric chain rather than alterations in which the molecule dimerized.

Location and Structural Analysis of Avidity Enhancing Mutations

Figures 11A, 11B:
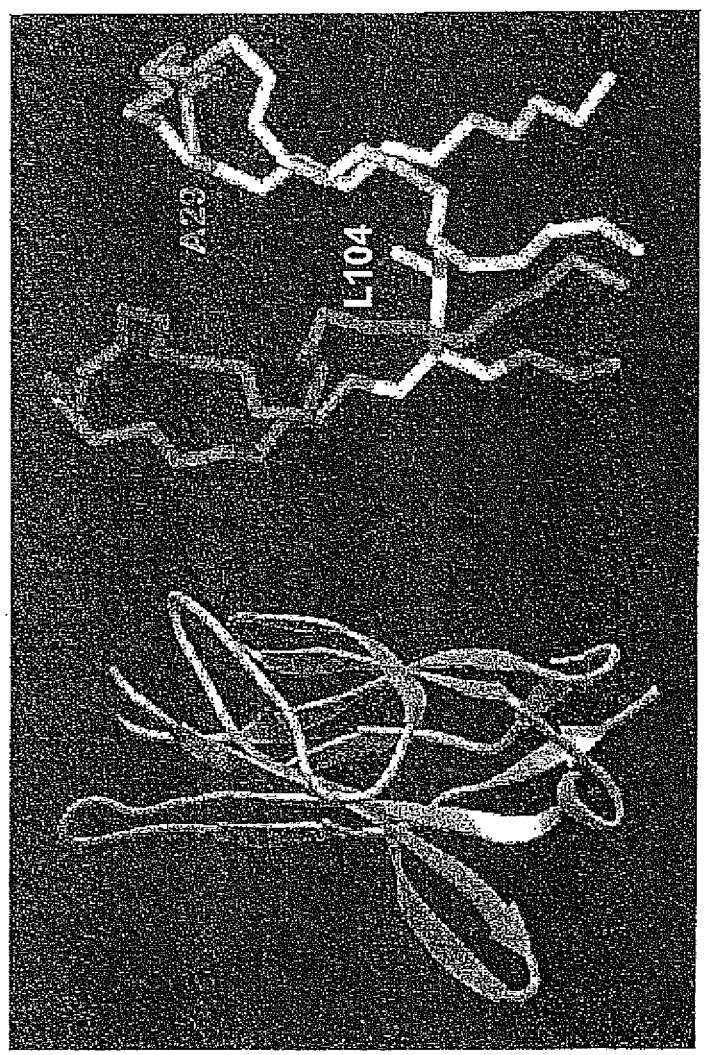
FIG. 11A illustrates a ribbon diagram of the CTLA4 extracellular Ig V-like fold generated from the solution structure determined by NMR spectroscopy.
FIG. 11B shows an expanded view of the S25-R33 region and the MYPPPY region (SEQ ID NO:9) indicating the location and side-chain orientation of the avidity enhancing mutations, L104 and A29.
Figure 12:
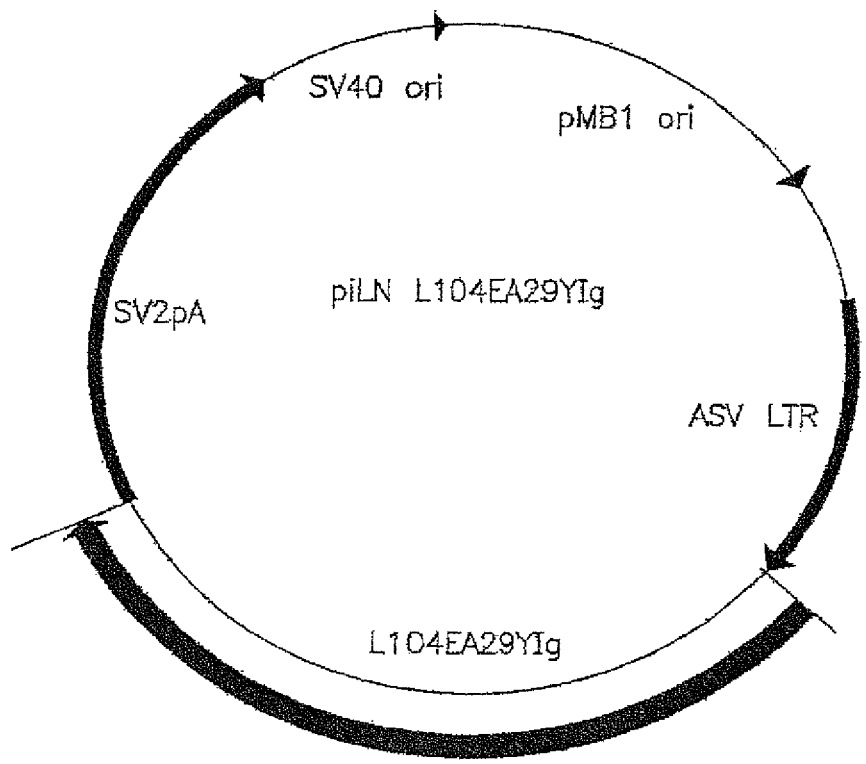
FIG. 12 depicts a schematic diagram of a vector, piLN-L104EA29Y, having the L104EA29YIg insert.

The solution structure of the extracellular IgV-like domain of CTLA4 has recently been determined by NMR spectroscopy (Metzler et al., (1997) *Nature Struct. Biol.,* 4:527-531. This allowed accurate location of leucine 104 and alanine 29 in the three dimensional fold (FIG. 11A-B). Leucine 104 is situated near the highly conserved MYPPPY amino acid sequence (SEQ ID NO:9). Alanine 29 is situated near the C-terminal end of the S25-R33 region, which is spatially adjacent to the MYPPPY region (SEQ ID NO:9). While there is significant interaction between residues at the base of these two regions, there is apparently no direct interaction between L104 and A29 although they both comprise part of a contiguous hydrophobic core in the protein. The structural consequences of the two avidity enhancing mutants were assessed by modeling. The A29Y mutation can be easily accommodated in the cleft between the S25-R33 region and the MYPPPY region (SEQ ID NO:9), and may serve to stabilize the conformation of the MYPPPY region (SEQ ID NO:9). In wild type CTLA4, L104 forms extensive hydrophobic interactions with L96 and V94 near the MYPPPY region (SEQ ID NO:9). It is highly unlikely that the glutamic acid mutation adopts a conformation similar to that of L104 for two reasons. First, there is insufficient space to accommodate the longer glutamic acid side chain in the structure without significant perturbation to the S25-R33 region. Second, the energetic costs of burying the negative charge of the glutamic acid side chain in the hydrophobic region would be large. Instead, modeling studies predict that the glutamic acid side chain flips out on to the surface where its charge can be stabilized by solvation. Such a conformational change can easily be accommodated by G105, with minimal distortion to other residues in the regions.

Binding of High Avidity Mutants to CHO Cells Expressing CD80 or CD86

FACS analysis (FIG. 2) of CTLA4Ig and mutant molecules binding to stably transfected CD80+ and CD86+CHO cells was performed as described herein. CD80-positive and CD86-positive CHO cells were incubated with increasing concentrations of CTLA4Ig, L104EA29YIg, or L104EIg, and then washed. Bound immunoglobulin fusion protein was detected using fluorescein isothiocyanate-conjugated goat anti-human immunoglobulin.

As shown in FIG. 2, CD80-positive or CD86-positive CHO cells ($1.5\times10^5$) were incubated with the indicated concentrations of CTLA4Ig (closed squares), L104EA29YIg (circles), or L104EIg (triangles) for 2 hr. at 23° C., washed, and incubated with fluorescein isothiocyanate-conjugated goat anti-human immunoglobulin antibody. Binding on a total of 5,000 viable cells was analyzed (single determination) on a FACScan, and mean fluorescence intensity (MFI) was determined from data histograms using PC-LYSYS. Data were corrected for background fluorescence measured on cells incubated with second step reagent only (MFI=7). Control L6 mAb (80 μg/ml) gave MFI<30. These results are representative of four independent experiments.

Binding of L104EA29YIg, L104EIg, and CTLA4Ig to human CD80-transfected CHO cells is approximately equivalent (FIG. 2A). L104EA29YIg and L104EIg bind more strongly to CHO cells stably transfected with human CD86 than does CTLA4Ig (FIG. 2B).

Functional Assays

Human CD4-positive T cells were isolated by immunomagnetic negative selection (Linsley et al., (1992) *J. Exp. Med.* 176:1595-1604). Isolated CD4-positive T cells were stimulated with phorbal myristate acetate (PMA) plus CD80-positive or CD86-positive CHO cells in the presence of titrating concentrations of inhibitor. CD4-positive T cells ($8\text{-}10\times10^4$/well) were cultured in the presence of 1 nM PMA with or without irradiated CHO cell stimulators. Proliferative responses were measured by the addition of 1 μCi/well of [3H]thymidine during the final 7 hours of a 72 hour culture. Inhibition of PMA plus CD80-positive CHO, or CD86-positive CHO, stimulated T cells by L104EA29YIg and CTLA4Ig was performed. The results are shown in FIG. 3. L104EA29YIg inhibits proliferation of CD80-positive PMA treated CHO cells more than CTLA4Ig (FIG. 3A). L104EA29YIg is also more effective than CTLA4Ig at inhibiting proliferation of CD86-positive PMA treated CHO cells (FIG. 3B). Therefore, L104EA29YIg is a more potent inhibitor of both CD80- and CD86-mediated costimulation of T cells.

FIG. 4 shows inhibition by L104EA29YIg and CTLA4Ig of allostimulated human T cells prepared above, and further allostimulated with a human B lymphoblastoid cell line (LCL) called PM that expressed CD80 and CD86 (T cells at $3.0\times10^4$/well and PM at $8.0\times10^3$/well). Primary allostimulation occurred for 6 days, then the cells were pulsed with $^3$H-thymidine for 7 hours, before incorporation of radiolabel was determined.

Secondary allostimulation was performed as follows. Seven day primary allostimulated T cells were harvested over lymphocyte separation medium (LSM) (ICN, Aurora, Ohio) and rested for 24 hours. T cells were then restimulated (secondary), in the presence of titrating amounts of CTLA4Ig or L104EA29YIg, by adding PM in the same ratio as above. Stimulation occurred for 3 days, then the cells were pulsed with radiolabel and harvested as above. The effect of L104EA29YIg on primary allostimulated T cells is shown in FIG. 4A. The effect of L104EA29YIg on secondary allostimulated T cells is shown in FIG. 4B. L104EA29YIg inhibits both primary and secondary T cell proliferative responses better than CTLA4Ig.

To measure cytokine production (FIG. 5), duplicate secondary allostimulation plates were set up. After 3 days, culture media was assayed using ELISA kits (Biosource, Camarillo, Calif.) using conditions recommended by the manufacturer. L104EA29YIg was found to be more potent than CTLA4Ig at blocking T cell IL-2, IL-4, and γ-IFN cytokine production following a secondary allogeneic stimulus (FIGS. 5A-C).

The effects of L104EA29YIg and CTLA4Ig on monkey mixed lymphocyte response (MLR) are shown in FIG. 6. Peripheral blood mononuclear cells (PBMC'S; $3.5\times10^4$ cells/well from each monkey) from 2 monkeys were purified over lymphocyte separation medium (LSM) and mixed with 2 g/ml phytohemaglutinin (PHA). The cells were stimulated 3 days then pulsed with radiolabel 16 hours before harvesting. L104EA29YIg inhibited monkey T cell proliferation better than CTLA4Ig.

TABLE I

Equilibrium and apparent kinetic constants are given in the following table (values are means ± standard deviation from three different experiments):

| Immobilized Protein | Analyte | $k_{on}$ (×10$^5$) M$^{-1}$ S$^{-1}$ | $k_{off}$ (×10$^{-3}$) S$^{-1}$ | $K_d$ nM |
|---|---|---|---|---|
| CD80Ig | CTLA4Ig | 3.44 ± 0.29 | 2.21 ± 0.18 | 6.51 ± 1.08 |
| CD80Ig | L104EIg | 3.02 ± 0.05 | 1.35 ± 0.08 | 4.47 ± 0.36 |
| CD80Ig | L104EA29YIg | 2.96 ± 0.20 | 1.08 ± 0.05 | 3.66 ± 0.41 |
| CD80Ig | CTLA4X$_{C120S}$ | 12.0 ± 1.0 | 230 + 10 | 195 ± 25 |
| CD80Ig | L104EA29YX$_{C120S}$ | 8.3 ± 0.26 | 71 ± 5 | 85.0 ± 2.5 |
| CD86Ig | CTLA4Ig | 5.95 ± 0.57 | 8.16 ± 0.52 | 13.9 ± 2.27 |
| CD86Ig | L104EIg | 7.03 ± 0.22 | 4.26 ± 0.11 | 6.06 ± 0.05 |
| CD86Ig | L104EA29YIg | 6.42 ± 0.40 | 2.06 ± 0.03 | 3.21 ± 0.23 |
| CD86Ig | CTLA4X$_{C120S}$ | 16.5 ± 0.5 | 840 ± 55 | 511 ± 17 |
| CD86Ig | L104EA29YX$_{C120S}$ | 11.4 ± 1.6 | 300 ± 10 | 267 ± 29 |

TABLE II

The effect on CD86Ig binding by mutagenesis of CTLA4Ig at the sites listed was determined by SPR, described supra. The predominant effect is indicated with a "+" sign.

| | Effects of Mutagenesis | | |
|---|---|---|---|
| Mutagenesis Site | No Apparent Effect | Slow "on" rate/slow "off rate | Reduced ligand binding |
| S25 | | + | |
| P26 | + | | |
| G27 | + | | |
| K28 | + | | |
| A29 | | + | |
| T30 | | + | |
| E31 | | | + |
| R33 | | | + |
| K93 | | + | |
| L96 | | + | |
| M97 | | | + |
| Y98 | | | + |
| P99 | | | + |
| P100 | | | + |
| P101 | | | + |
| Y102 | | | + |
| Y103 | | + | |
| L104 | | + | |
| G105 | | | + |
| I106 | + | | |
| G107 | + | | |
| Q111 | + | | |
| Y113 | + | | |
| I115 | + | | |

As will be apparent to those skilled in the art to which the invention pertains, the present invention may be embodied in forms other than those specifically disclosed above without departing from the spirit or essential characteristics of the invention. The particular embodiments of the invention described above, are, therefore, to be considered as illustrative and not restrictive. The scope of the present invention is as set forth in the appended claims rather than being limited to the examples contained in the foregoing description.

What is claimed is:

1. A CTLA4 mutant molecule which binds CD80 and/or CD86 comprising an extracellular domain of CTLA4 as shown in SEQ ID NO:8 beginning with alanine at position 26 or methionine at position 27 and ending with aspartic acid at position 150, wherein in the extracellular domain an alanine at position 55 is substituted with an amino acid selected from the group consisting of leucine, tryptophan, and threonine, and a leucine at position 130 is substituted with a glutamic acid.

2. The CTLA4 mutant molecule of claim 1 further comprising an amino acid sequence which alters the solubility, affinity or valency of the soluble CTLA4 mutant molecule.

3. The CTLA4 mutant molecule of claim 2, wherein the amino acid sequence comprises a human immunoglobulin constant region.

4. The CTLA4 mutant molecule of claim 3 wherein the immunoglobulin constant region is mutated to reduce effector function.

5. The CTLA4 mutant molecule of claim 3 wherein the immunoglobulin constant region comprises a hinge, CH2 and CH3 regions of an immunoglobulin molecule.

6. A CTLA4 mutant molecule which binds CD80 and/or CD86 comprising an extracellular domain of CTLA4 as shown in SEQ ID NO:6 beginning with alanine at position 26 or methionine at position 27 and ending with aspartic acid at position 150, wherein in the extracellular domain an alanine at position 55 is substituted with an amino acid selected from the group consisting of leucine, tryptophan, and threonine.

7. The CTLA4 mutant molecule of claim 6 wherein in the extracellular domain an alanine at position 55 is substituted with leucine.

8. The CTLA4 mutant molecule of claim 6 wherein in the extracellular domain an alanine at position 55 is substituted with tryptophan.

9. The CTLA4 mutant molecule of claim 6 wherein in the extracellular domain an alanine at position 55 is substituted with threonine.

10. A method for regulating a T cell interaction with a CD80 and/or CD86 positive cell comprising contacting the CD80 and/or CD86 positive cell with the soluble CTLA4 mutant molecule of claim 1 so as to form a CTLA4 mutant molecule/CD80 or a CTLA4 mutant molecule/CD86 complex, the complex interfering with interaction between the CTLA4-positive T cell and the CD80 and/or CD86 positive cell.

11. The method of claim 10, wherein the CD80 and/or CD86 positive cell is an antigen presenting cell.

12. The method of claim 11, wherein the interaction of the CTLA4-positive T cells with the CD80 and CD86 positive cells is inhibited.

13. A method for inhibiting graft versus host disease in a subject which comprises administering to the subject the soluble CTLA4 mutant molecule of claim 1 and a ligand reactive with IL-4.

14. A pharmaceutical composition for treating an immune system disease comprising a pharmaceutically acceptable carrier and the soluble CTLA4 mutant molecule of claim 1.

* * * * *